United States Patent [19]

King et al.

[11] Patent Number: 5,587,458

[45] Date of Patent: Dec. 24, 1996

[54] ANTI-ERBB-2 ANTIBODIES, COMBINATIONS THEREOF, AND THERAPEUTIC AND DIAGNOSTIC USES THEREOF

[75] Inventors: C. Richter King; Philip G. Kasprzyk, both of Washington, D.C.; Robert E. Bird, Rockville, Md.

[73] Assignee: Aronex Pharmaceuticals, Inc., The Woodlands, Tex.

[21] Appl. No.: 61,092

[22] Filed: May 14, 1993

Related U.S. Application Data

[63] Continuation-in-part of Ser. No. 906,555, Jun. 30, 1992, which is a continuation-in-part of Ser. No. 772,270, Oct. 7, 1991, abandoned.

[51] Int. Cl.$^6$ .......................... C07K 16/00; C07K 16/46; C07K 16/28
[52] U.S. Cl. ..................... 530/387.3; 530/387.7; 530/388.22; 530/389.7; 530/391.3; 530/391.7; 436/501; 436/512
[58] Field of Search .............. 530/387.1, 387.3, 530/387.7, 388.1, 388.22, 388.8, 389.7, 391.1, 391.3, 391.7, 388.85, 409, 866, 367, 370, 300, 350; 424/86.91, 130.1, 133.1, 134.1, 135.1, 138.1, 141.1, 143.1, 155.1, 156.1, 192.1, 193.1; 436/501, 502, 536; 425/7.92, 7.1, 183

[56] References Cited

U.S. PATENT DOCUMENTS

| | | | |
|---|---|---|---|
| 4,704,692 | 11/1987 | Ladner | 364/496 |
| 4,867,973 | 9/1989 | Goers et al. | 424/85.91 |
| 4,939,666 | 7/1990 | Hardman | 364/496 |
| 4,946,778 | 8/1990 | Ladner et al. | 435/69.6 |

FOREIGN PATENT DOCUMENTS

| | | | |
|---|---|---|---|
| 2197323 | 5/1988 | United Kingdom | C07K 15/06 |

OTHER PUBLICATIONS

Waldman Science 252:1657–1662 (1991).
Harris et al. TIBTECH 11:42–46 (1993).
Osband et al. Immunotherapy 11(6):193–195(1990).
Dillman Ann. Internal Med. 111:592–603 (1989).
Hird et al. Genes and Cancer, by Wiley & Sons, ed. D. Carney et al. (1990) Chapter 17.
Langton et al. Cancer Res. 51(10):2593–2598 (1991).
Shepard et al. J. Clin. Imm. 11(3):117–127 (1991).
Ware et al. Human Pathology 2(3):254–258 (1991).
Lipponen et al. Eur.Urol. 20:238–242 (1991).
Dykins et al. J. Pathology 163:105–110 (1991).
Paik et al. J. Clin. Oncology 8(1):103–112 (1990).
Fendly et al. Can. Res. 50:1550–1558 (1990).
Drebin et al. Oncogene 2:273–277 (1988).
Riechmann et al. Nature 332:323–327 (1988).
Batra et al. Proc. Natl. Acad. Sci. 89:5867–5871 (1992).
Lenz et al. Gene 87:213–218 (1990).

*Primary Examiner*—Donald E. Adams
*Attorney, Agent, or Firm*—C. Steven McDaniel; Conley, Rose & Tayon, P.C.

[57] ABSTRACT

The present invention relates to novel antibodies, in particular monoclonal and single chain antibodies derived therefrom which specifically bind to erbB-2, as well as diagnostic and therapeutic uses thereof. The present invention also relates to a combination of at least two erbB-2 specific antibodies which are capable of preventing and treating human malignancies wherein the malignant cells overexpress gp185$^{erbB-2}$. The monoclonal antibodies of the combination preferably recognize different epitopes of the gp185 expression product of erbB-2, therefore, the antibodies do not cross react with each other. Preferably, the combination will provide for synergistic decrease in the expression of the erbB-2 gene product.

12 Claims, 10 Drawing Sheets

FIG. 7

```
ATGGACCTGCAGCTGACCCAGTCTCCAGCAATCCTGTCTGCATCTCCAGG
MetAspLeuGlnLeuThrGlnSerProAlaIleLeuSerAlaSerProGly

GGAGAAGGTCACAATGACTTGCAGGGCCACCCCAAGTGTAAGTTACATGC
 GluLysValThrMetThrCysArgAlaThrProSerValSerTyrMetHis

ACTGGTATCAGCAGAAGCCAGGATCCTCCCCCAAACCTTGGATTTATACC
 TrpTyrGlnGlnLysProGlySerSerProLysProTrpIleTyrThr

ACATCCAACCTKGCTTCTGGAGTCCCTGCTCGCTTCAGTGGCGGTGGGTC
 ThrSerAsnLeuAlaSerGlyValProAlaArgPheSerGlyGlyGlySer

TGGGACCTCTTACTCTCTCACAGTCAGCAGAGTGGAGGCTGAAGATGCTG
 GlyThrSerTyrSerLeuThrValSerArgValGluAlaGluAspAlaAla

CCACTTATTACTGCCAGCAGTGGAGTCGTAGCCCACCCACGTTCGGAGGG
 ThrTyrTyrCysGlnGlnTrpSerArgSerProProThrPheGlyGly

GGGTCCAAGCTGGAAATAAAAGGTTCTACCTCTGGTTCTGGTAAATCTTC
 GlySerLysLeuGluIleLysGlySerThrSerGlySerGlyLysSerSer

TGAAGGTAAAGGTGTGCAGCTGCAGGAGTCAGGACCTGAGGTGGTGAAGC
 GluGlyLysGlyValGlnLeuGlnGluSerGlyProGluValValLysPro

CTGGAGGTTCAATGAAGATATCCTGCAAGACTTCTGGTTACTCATTCACT
 GlyGlySerMetLysIleSerCysLysThrSerGlyTyrSerPheThr

GGCCACACCATGAACTGGGTGAAGCAGAGCCATGGAAAGAACCTTGAGTG
 GlyHisThrMetAsnTrpValLysGlnSerHisGlyLysAsnLeuGluTrp

GATTGGACTTATTAATCCTTACAATGGTGATACTAACTACAACCAGAAGT
 IleGlyLeuIleAsnProTyrAsnGlyAspThrAsnTyrAsnGlnLysPhe

TCAAGGGCAAGGCCACATTTACTGTAGACAAGTCGTCCAGCACAGCCTAC
 LysGlyLysAlaThrPheThrValAspLysSerSerSerThrAlaTyr

ATGGAGCTCCTCAGTCTGACATCTGAGGACTCTGCAGTCTATTACTGTGC
 MetGluLeuLeuSerLeuThrSerGluAspSerAlaValTyrTyrCysAla

AAGGAGGGTTACGGACTGGTACTTCGATGTCTGGGGCGCAGGGACCACGG
 ArgArgValThrAspTrpTyrPheAspValTrpGlyAlaGlyThrThrVal

TCACCGTCTCC
 ThrValSer
```

FIG. 8

```
ATGCAGCTGACCCAGTCTCCAGCAATCATGTCTGCATCTCCAGGGGAAAA    50
MetGlnLeuThrGlnSerProAlaIleMetSerAlaSerProGlyGluLys

GGTCACCATGACCTGCAGTGCCAGCTCAAGTGTAAGTAACATGCACTGGT    100
 ValThrMetThrCysSerAlaSerSerSerValSerAsnMetHisTrpTyr

ATCAGCAGAAGTCAAGCACCTCCCCCAAACTCTGGGTTTATGACACATCC    150
  GlnGlnLysSerSerThrSerProLysLeuTrpValTyrAspThrSer

AAACTGGCTTCTGGAGTCCCAGGTCGCTTCAGTGGCAGTGGGTCTGGAAA    200
LysLeuAlaSerGlyValProGlyArgPheSerGlySerGlySerGlyAsn

CTCTTACTCTCTCACGATCAGCAGCATGGAGGCTGAAGATGCTGCCACTT    250
 SerTyrSerLeuThrIleSerSerMetGluAlaGluAspAlaAlaThrTyr

ATTATTGTTATCAGGGGAGTGGGTACCCATTCACGTTCGGCTCGGGGACA    300
  TyrCysTyrGlnGlySerGlyTyrProPheThrPheGlySerGlyThr

AAGTTGGAAATAAAAGGTTCTACCTCCGGATCTGGTAAATCTTCTGAAGG    350
LysLeuGluIleLysGlySerThrSerGlySerGlyLysSerSerGluGly

TAAAGGTGTGCAGCTGCAGCAGTCTGGGGTTGAGCTTGTCCGAGGAGGGG    400
 LysGlyValGlnLeuGlnGlnSerGlyValGluLeuValArgGlyGlyAla

CCTTAGTCAAGTTGTCCTGCAAAGCTTCTGACTTCAACATTAAAGACTAT    450
   LeuValLysLeuSerCysLysAlaSerAspPheAsnIleLysAspTyr

TATATCCACTGGGTGAAGCAGAGGCCTGAACAGGGCCTGGAATGGATTGG    500
TyrIleHisTrpValLysGlnArgProGluGlnGlyLeuGluTrpIleGly

ATGGATTCATCCTGAGAATGGTAATACTGTATATGACCCGAAATTCCAGG    550
 TrpIleHisProGluAsnGlyAsnThrValTyrAspProLysPheGlnGly

GCAAGGCCAGTATAACAGCAGACACATCCTCCAACGCGGCCTACCTTCAG    600
  LysAlaSerIleThrAlaAspThrSerSerAsnAlaAlaTyrLeuGln

CTCAGCAGCCTGACATCTGAGGACACTGCCGTCTATTACTGTGCTTCTTA    650
LeuSerSerLeuThrSerGluAspThrAlaValTyrTyrCysAlaSerTyr

TTACTACTATAGTGCTTACTATGCTATGTACTACTGGGGTCAAGGAACCT    700
 TyrTyrTyrSerAlaTyrTyrAlaMetTyrTyrTrpGlyGlnGlyThrSer

CGGTCACCGTCTCCTCATAA     720
  ValThrValSerSerTer
```

ANTI-ERBB-2 ANTIBODIES, COMBINATIONS THEREOF, AND THERAPEUTIC AND DIAGNOSTIC USES THEREOF

The subject application is a continuation-in-part of U.S. Pat. Ser. No. 07/906,555, pending, filed on Jun. 30, 1992, which is itself a continuation-in-part of U.S. Pat. Ser. No. 07/772,270, filed on Oct. 7, 1991, abandoned. These applications are incorporated by reference in their entirety herein.

BACKGROUND OF THE INVENTION

This invention relates to novel antibodies capable of specifically binding to the erbB-2, $gp185^{erbB 2}$ gene product, and combinations thereof.

The invention further relates to the use of antibodies capable of binding to the erbB-2, and/or combinations thereof, for treating and/or preventing the formation of erbB-2 expressing tumors.

The invention also relates to the use of antibodies capable of binding to the erbB-2 gene product, and/or combinations thereof, for the immunological detection of erbB-2 expressing tumor cells in an analyte.

The invention further relates to conjugates comprising novel antibodies capable of binding to $gp185^{erbB-2}$, and combinations thereof, wherein the antibody is bound to a cytotoxic moiety or a label which provides for the detection thereof, e.g., a fluorescent, enzymatic or radiolabel.

In particular, the invention relates to the use of monoclonal antibodies capable of specifically binding to $gp185^{erbB-2}$, and/or combinations thereof, and/or single chain antibodies derived therefrom for the treatment and/or prevention of erbB-2 expressing tumors. Additionally, the invention relates to the use of specific monoclonal antibodies or single chain antibodies capable of specifically binding to $gp185^{erbB-2}$ for the detection of erbB-2 expressing tumor cells.

In recent years, evidence has been accumulated that growth factors and their receptors may be involved in the process of malignant transformation. The erbB-2 gene product (also called HER2, neu or c-erbB-2) encodes a 185-kDa growth factor receptor which has been implicated in the malignancy of some human adenocarcinomas. Specifically, the erbB-2 protein, $gp185^{erbB-2}$, is a receptor tyrosine kinase (Yarden et al, Ann. Rev. Biochem., (1988), 57, 443–478) which is homologous to the epidermal growth factor (EGF) receptor. (Coussens et al, Science, (1985), 230, 1132–1139; Yamamoto et al., Nature, (1986), 319, 230–234.) The rat homologue of the gene undergoes oncogenic activation through a single point mutation. (Bargmann et al, Cell, (1986), 45, 649–657.)

The erbB-2 protein, like other receptor proteins, is composed of extracellular, transmembrane and intracellular domains. The extracellular domain contains two cysteine-rich areas and is 44% homologous to the epidermal growth factor receptor (EGFR). The intracellular domain contains a tyrosine kinase which is 82% homologous to that of EGFR. Because of these similarities to EGFR and to other tyrosine kinase receptors, it has been suggested in the literature that the c-erbB-2 protein may function as a growth factor receptor.

Clinical and experimental evidence suggests a role for overexpression of the erbB-2 protein in the progression of human breast, ovarian, and non-small lung carcinoma. For example, amplification and/or overexpression of the erbB-2 gene have been shown in 20–30% of breast adenocarcinomas (King et al, Science, (1985), 229, 974–976; Slamon et al, Science, (1987), 235, 177–182; Slamon et al, Science, (1989), 244, 707–712; Yokota et al, Lancet, (1986), 1,765–767; King et al, Cancer Res., (1985), 49, 4185–4191), ovary adenocarcinomas (Slamon et al, Science, (1989), 244, 707–712), lung adenocarcinomas (Schneider et al, Cancer Res., (1989), 49, 4968–4971) and stomach adenocarcinomas (Park et al, Cancer Res., (1989), 49, 6605–6609). In breast carcinoma, a correlation has been observed between gene amplification and overexpression of erbB-2 protein and the aggressiveness of the malignancy (Slamon et al, Science, (1987), 237, 177–182; Slamon et al, Science, (1989), 244, 707–712). In cases of gene amplification, there is a resulting 50- to 100-fold increase in erbB-2 in RNA compared with normal cell levels (Kraus et al, EMBO J., (1987), 6, 605–610). The overexpression of erbB-2 has also been directly linked to the malignant conversion of cancer cells. (DiFiore et al, Science, (1986), 237, 178–182; Hudziak et al, Proc. Nat'l. Acad. Sci., (1987), 89, 7159–7163).

At least two lines of evidence suggest that erbB-2 overexpression may be involved in the pathogenesis of human neoplasia. First, as discussed supra, overexpression has been linked with poor prognosis in breast cancer, as well as ovarian cancer (Slamon et al, Science, (1989), 244, 707–712; Berchuk et al, Cancer Res., (1990), 50, 4087–4091), stomach cancer (Yonemura et al, Cancer Res., (1991), 51, 1004–1032) and lung cancer (Kern et al, Cancer Res., (1990), 50, 5184–5191). Second, artificial overexpression of erbB-2 induces a transformed phenotype in NIH 3T3 fibroblasts (DiFiore et al, Science, (1986), 237, 178–182; Hudziak et al, Proc. Nat'l. Acad. Sci., (1987), 84, 7159–7163), as well as in mammary epithelial cells (Pierce et al, Oncogene, (1991), 6, 1189–1194), suggesting that overexpression can not contribute directly to the development of the malignant phenotype.

Because of the extensive homology between the erbB-2 protein and the EGFR, it is widely assumed that the activation of growth signal transduction may proceed through similar mechanisms. One proposed mechanism involves receptor dimerization or oligomerization, which is thought to be an important step in the activation of EGFR intrinsic tyrosine kinase function (Yarden et al, Biochemistry, (1988), 27, 3114–3118; Schlessinger, Biochemistry, (1988), 27, 3119–3123). Interfering with receptor-receptor interactions has been evaluated as a potential therapeutic approach for the treatment of cancers associated with erbB-2 overexpression. In particular, such studies have involved the use of single monoclonal antibodies directed against the erbB-2 protein (Hudziak et al, Mol. Cell. Biol., (1989), 9, 1165–1172) and the related EGFR protein (Divgi et al, J. Nat'l. Cancer Inst., (1991), 83, 97–104) as potential therapeutic agents for the treatment of cancer.

The potential use of monoclonal antibodies for diagnosis and treatment of cancer has been studied extensively (Mellstadt, Curr. Opinion Immunol., (1990), 2, 708–713). Receptors for growth factors constitute a desirable target for this approach because their location on the cell membrane renders them accessible to antibody molecules. Moreover, antibodies directed to growth factor receptors can potentially block biological functions essential for cell proliferation.

Previous studies have demonstrated in animal systems the potential therapeutic effects of monoclonal antibodies against the EGFR (Matsui et al, Cancer Res., (1984), 44, 1002–1007; Aboud-Pirak et al, J. Nat'l. Cancer Inst., (1988), 80, 1605–1611). Also, different monoclonal antibodies to the erbB-2 receptor have been found to inhibit the proliferation of a human breast carcinoma cell line in human tissue culture (Hudziak et al, *Mol. Cell. Biol.*, (1989), 9, 1165–1172), and an antibody directed to the rat erbB-2 protein, has been reported to inhibit the tumorigenicity of fibroblasts transformed by the mutant rat erbB-2 oncogene (Drebin et al, *Proc. Nat'l. Acad. Sci.*, (1986), 83, 9126–9133; Drebin et al, *Oncogene*, (1988), 2, 387–399). Additionally, monoclonal antibodies which bind to erbB-2 have been used to study the biological function of the presumed receptor (McKenzie et al, *Oncogene*, (1989), 4, 543–548); Van Leenwen et al, *Oncogene*, (1990), 5,497,503; Fendly et al, *Cancer Res.* (1990), 50, 1550–1558).

While some monoclonal antibodies to the erbB-2 protein have shown promise as potential anticancer therapeutic agents, variable effects are observed dependent upon the particular monoclonal antibody. For example, Stancovski et al studied the in vivo effects of monoclonal antibodies on erbB-2 expressing tumors. Although some of the administered antibodies almost completely inhibited the growth in athymic mice of transfected murine fibroblasts that overexpress the erbB-2 protein, other antibodies were found to accelerate tumor growth or to result in intermediate responses (Stancovski et al, *Proc. Nat'l. Acad. Sci.*, (1991), 88, 8691–8695). Based on the variable observed effects, Stancovski et al postulated that anti-erbB-2 antitumor antibodies may affect both receptor functioning and host-tumor interactions.

Recently, the construction and bacterial expression of a bifunctional single chain antibody-phosphatase fusion protein targeted to the human erbB-2 receptor was reported by Weis et al, *Biotechnology*, (1992), 10, 1128–1132. Wels et al, reported that this fusion protein exhibits sufficient binding affinity to cells expressing the erbB-2 receptor to permit the use thereof as an immunohistochemical reagent for the detection of erbB-2 antigen on cells or tissues.

SUMMARY OF THE INVENTION

One object of the invention is to provide novel antibodies, preferably monoclonal or single chain antibodies derived therefrom, capable of specifically binding to erbB-2 protein, $gp185^{erbB-2}$, and which do not substantially bind to normal human cells which may be utilized for the treatment or prevention of erbB-2 expressing tumor cells, or for the immunological detection of erbB-2 expressing tumor cells.

Another object of the present invention is to provide a novel combination of antibodies comprising at least two different antibodies, preferably monoclonal or single chain antibodies which are capable of specifically binding to an extracellular domain of the erbB-2 protein, which antibodies are separately capable of treating and/or preventing the growth of human tumors associated by the overexpression of erbB-2, and wherein the combination results in greater cytotoxic activity than expected for the sum of the individual antibodies at the same overall antibody concentration.

Still another object of the invention is to provide novel therapeutic or diagnostic conjugates comprising anti-erbB-2 antibodies which are attached to a cytotoxic or detectable moiety.

Another object of the invention is to provide anti-tumor pharmaceutical compositions comprising an anti-tumor effective amount of the novel anti-erbB-2 specific antibodies or combinations thereof.

Another object of the invention is to provide immunodiagnostic compositions which comprise the novel anti-erbB-2 antibodies of the invention, preferably in combination with a moiety which provides for the detection thereof.

Still another object of the invention is to provide methods for the treatment and/or prevention of erbB-2 receptor overexpressing tumors comprising the administration of an anti-tumor effective amount of at least one of the disclosed anti-erbB-2 specific antibodies, or combination of erbB-2 specific antibodies. Preferably, such combinations of erbB-2 antibodies will exhibit better cytotoxic activity than would be expected for the sum of the cytotoxic activity of the individual antibodies at the same overall antibody concentration. Additionally, one or more of the administered antibodies may be conjugated to a cytotoxic moiety, e.g., an anti-tumor drug, toxin, or radionuclide.

Yet another object of the invention is to provide methods for the use of the disclosed erbB-2 binding antibodies and conjugates thereof for the immunological detection of erbB-2 expressing tumor cells.

DETAILED DESCRIPTION OF THE DRAWINGS

Figure 1A:

FIG. 1A. Specificity of monoclonal antibodies e21 and e23. Subconfluent SK-Br-3 monolayers were metabolically labeled with 355S-Cys (spec. act. 1000 Ci/mmol). Total cell proteins were immunoprecipitated with 10 µg of the indicated antibodies. The immune complexes were recovered by Protein G Agarose (Genex, Gaithersburg, Md.) and analyzed by SDS-PAGE on an 8–16% Tris-Glycine gel. The gel was exposed to film at −70° C. overnight with an intensifying screen.

Figure 1B:
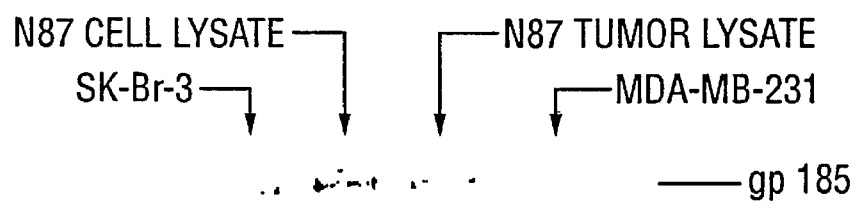

FIG. 1B. $gp185^{erbB-2}$ overexpression in the gastric cell line N87 and a tumor from N87 mouse xenografts compared to high and low $gp185^{erbB-2}$ overexpressers. Cells or tumor were lysed in sample buffer which contained 0.125 M Tris-HCl, 4% SDS, 0.002% bromophenol blue, and 15% glycerol. 5% β-mercaptoethanol was added after the protein concentration was determined. Samples (10 µg total protein) were boiled for 3 min, fractionated by SDS-PAGE on 8–16% Tris-Glycine gel and transferred to nitrocellulose. Detection of $gp185^{erbB-2}$ was performed with a monoclonal antibody to the c-terminal portion of the protein.

Figure 1C:
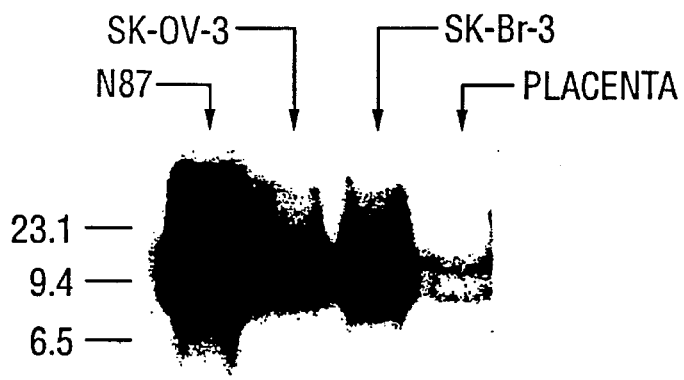

FIG. 1C. Southern blot analysis of the erbB-2 gene in N87 (gastric), SK-Br-3 (breast), and SK-OV-3 (ovarian) cell lines and human placenta. DNA was extracted from cell lines and human placenta tissue using guanidine thiocyanate and cesium gradient centrifugation. DNA (15 µg) was cleaved with restriction enzyme HindIII, separated by electrophoresis on a 1% agarose gel, transferred to nitrocellulose, and probed with radioactive erbB-2 cDNA probe as previously described in King et al, *Cancer Res.* (1989), 49, 4185. The cDNA probe corresponds to the entire erbB-2 protein coding region.

Figure 2:
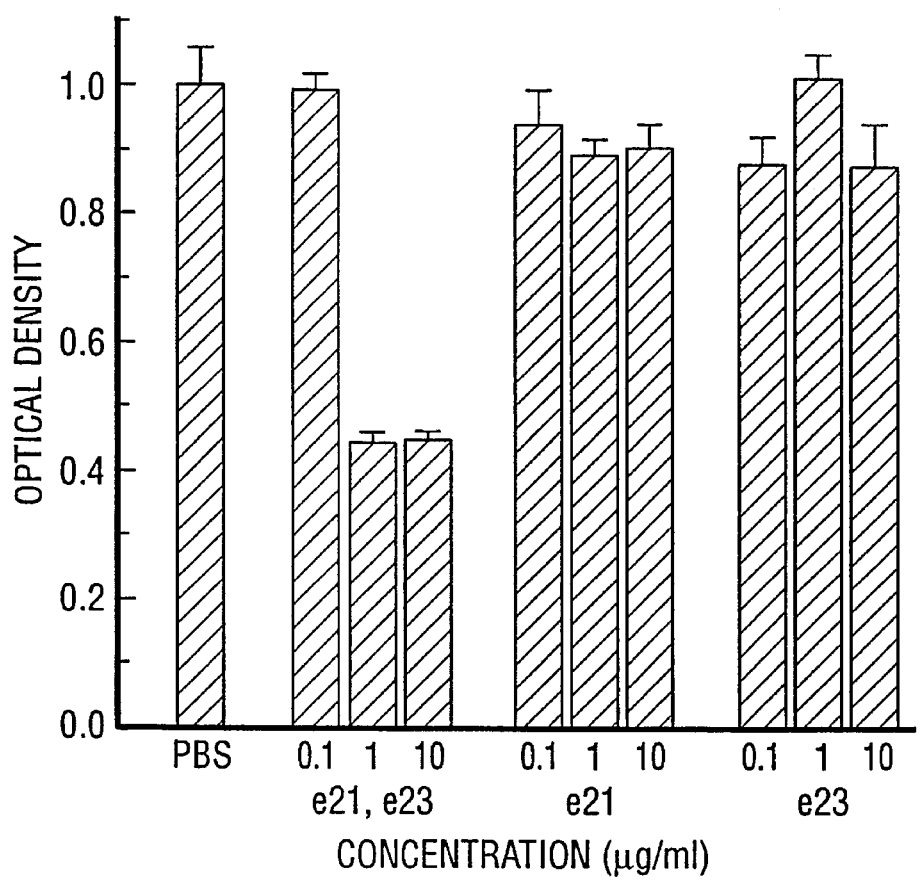

FIG. 2. Effects of e21 and e23 on the growth of human N87 transferrin (10 µg/ml), 17-β-estradiol (10 nM), sodium selenite (5 nM), and 10 mM Hepes. PBS, e21, e23 or a combination of e21 and e23 at the indicated concentration were then added. The plates were grown at 37° C. in a 5% $CO_2$ humidified atmosphere. After 7 days, 50 µl of 3-(4,5-dimethylthiazol-2-yl)-2,5-diphenyl tetrazolium bromide (0.1 mg) were added and allowed to incubate for 4 hours at 37° C. 90% of the media was then removed and the crystals solubilized in 0.175 ml DMSO. Optical densities were measured at 540 nm in a Molecular Devices Vmax kinetic microplate reader. Results are the average of eight wells with standard deviations noted. Under the conditions used, the cell number is directly proportional to MTT reduction.

Figure 3A:
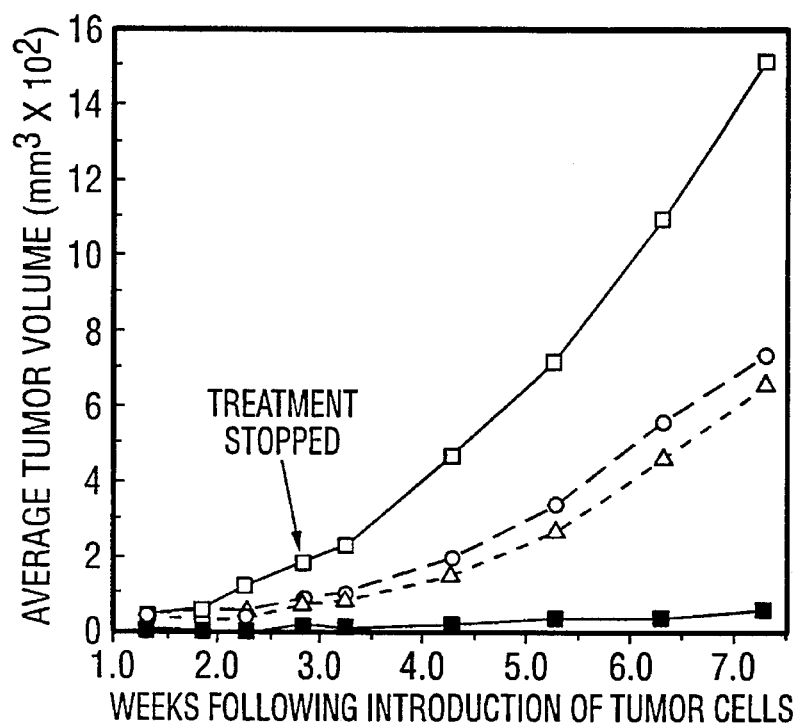

FIG. 3A. Effects of treatment with e21, e23, a combination of e21 and e23, or PBS on the growth of N87 tumor xenografts in BNX mice. Tumor cells ($5\times10^6$/mouse) were subcutaneously injected into the flanks of BNX (beige, nude, xid) mice. Treatment begun on day 1 consisted of four trial groups (3 mice per group) each given 0.2 ml intraperitoneal injections twice a week of either PBS, 200 µg purified e21 (0), 200 µg purified e23, or a mixture of 100/µg purified e21 and 100 µg of purified e23 for three weeks. Tumor growth is reported as an average relative tumor volume, s.e.m. ±15%. Two repeats of the experiment gave the same results.

Figure 3B:
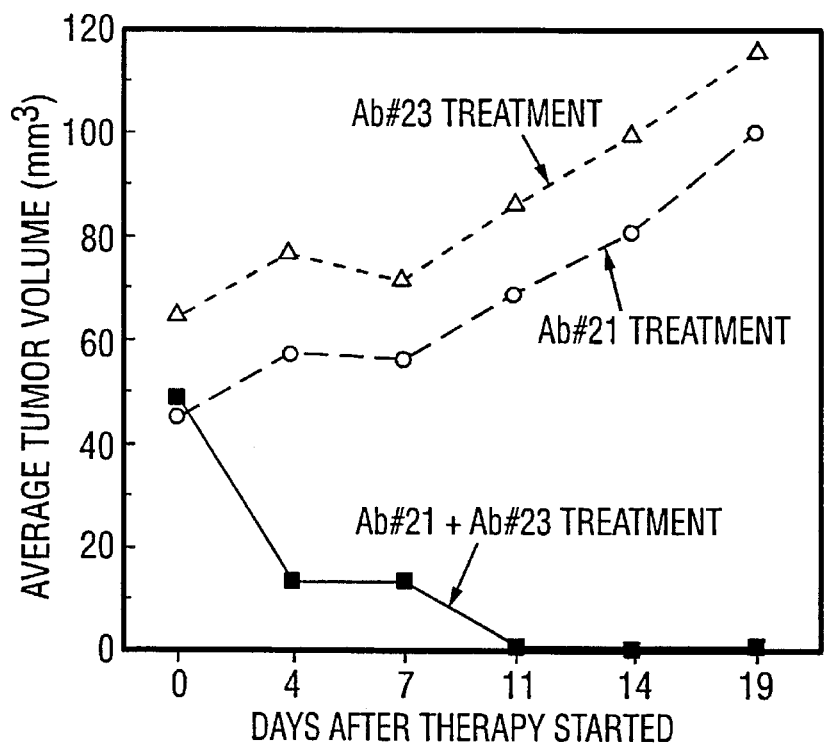

FIG. 3B. Effect of treatment after the formation of small tumors. Cells were injected using the same treatment protocol as above except for the fact the treatment was begun 4 days after cell injection instead of 1 day after. Animal care was in accordance with institutional guidelines.

Figure 4A:
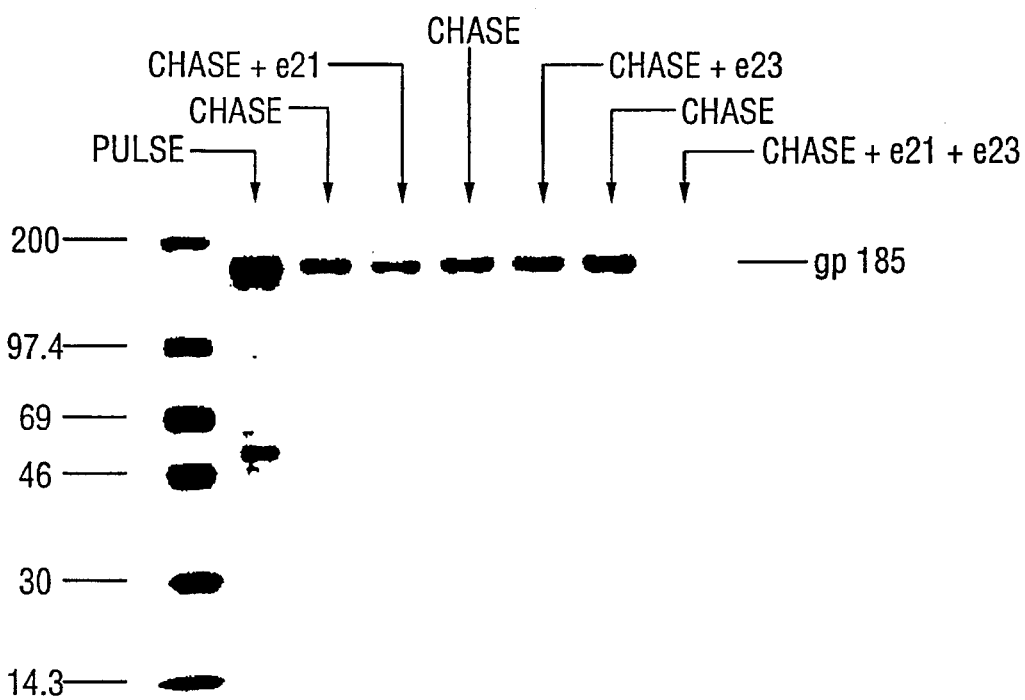

FIG. 4A. Effect of antibody binding on erbB-2 protein turnover. Subconfluent N87 cell monolayers were pulse-labeled 1 h with 20 µCi $^{35}$S-Cysteine and then chased with 5 mM Cys in the presence of e21 alone, e23 alone, or a 1:1 combination of e21 and e23 (10 µg/ml) for 24 h. Total cellular protein was immunoprecipitated as described in FIG. 1 using a monoclonal antibody directed against the c-terminus of gp185$^{erbB-2}$ coupled to Sepharose and analyzed by SDS-PAGE. The gel was exposed to film at −70° C. overnight with an intensifying screen.

Figure 4B:
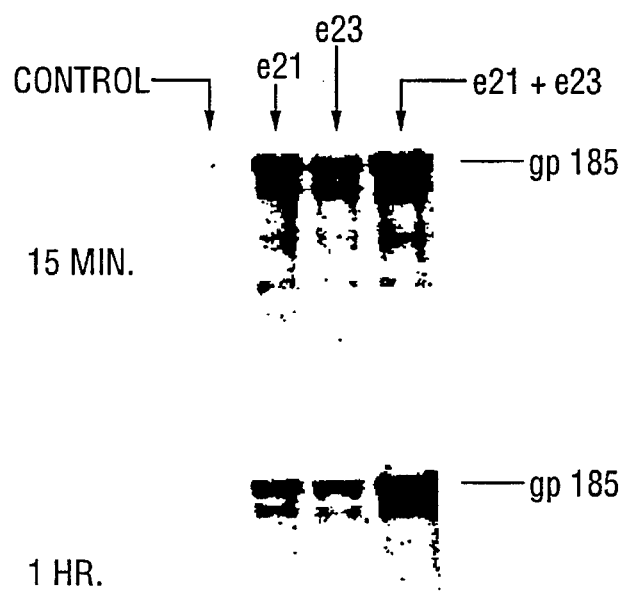

FIG. 4B. Measurement of tyrosine phosphorylation of gp185$^{erbB-2}$ after incubation with antibody combination. Cells were plated as described in the Materials and Methods infra. After 1 h cells were processed as described infra. Proteins were then electroblotter onto nitrocellulose paper and incubated with anti-phosphotyrosine IgG (monoclonal; Upstate Biotechnology, Inc.) and immunodetected using $^{125}$I-protein A. The gel was exposed to film at −70° C. overnight with an intersifying screen.

Figure 5:
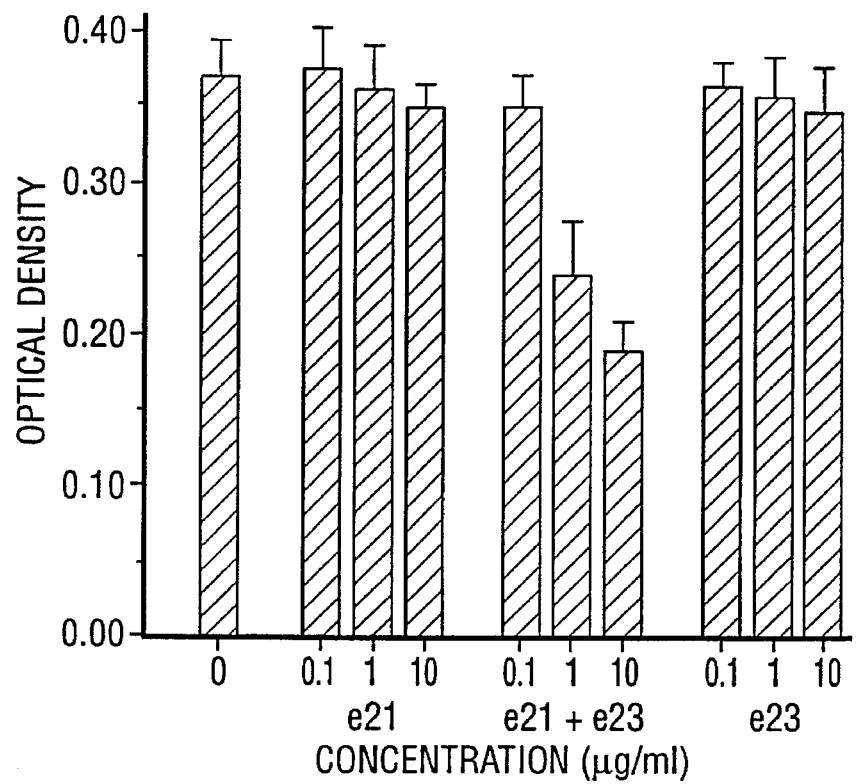

FIG. 5. Effects of e21 and e23 on the growth of human Calu-3 lung adenocarcinoma tumor cells in a monolayer MTT growth assay. A single cell suspension of 10,000 cells/well was plated in a chemically defined medium consisting of RPMI-1640 supplemented with insulin (5 µg/ml), human transferrin (10 µg/ml), 17-β-estradiol (10 nM), sodium selenite (5 nM, and 10 mM Hepes. PBS, e21, e23 or a combination of e21 and e23 at the indicated concentration were then added. The plates were grown at 37° C. in a 5% $CO_2$ humidified atmosphere. After 7 days, 50 µl of 3-(4,5-dimethylthiazol-2-yl)-2,5-diphenyl tetrazolium bromide (0.1 mg) were added and allowed to incubate for 4 hours at 37° C. 90% of the media was then removed and the crystals solubilized in 0.175 ml DMSO. Optical densities were measured at 540 nm in a Molecular Devices Vmax kinetic microplate reader. Results are the average of eight wells with standard deviations noted. Under the conditions used, the cell number is directly proportional to MTT reduction.

Figure 6:
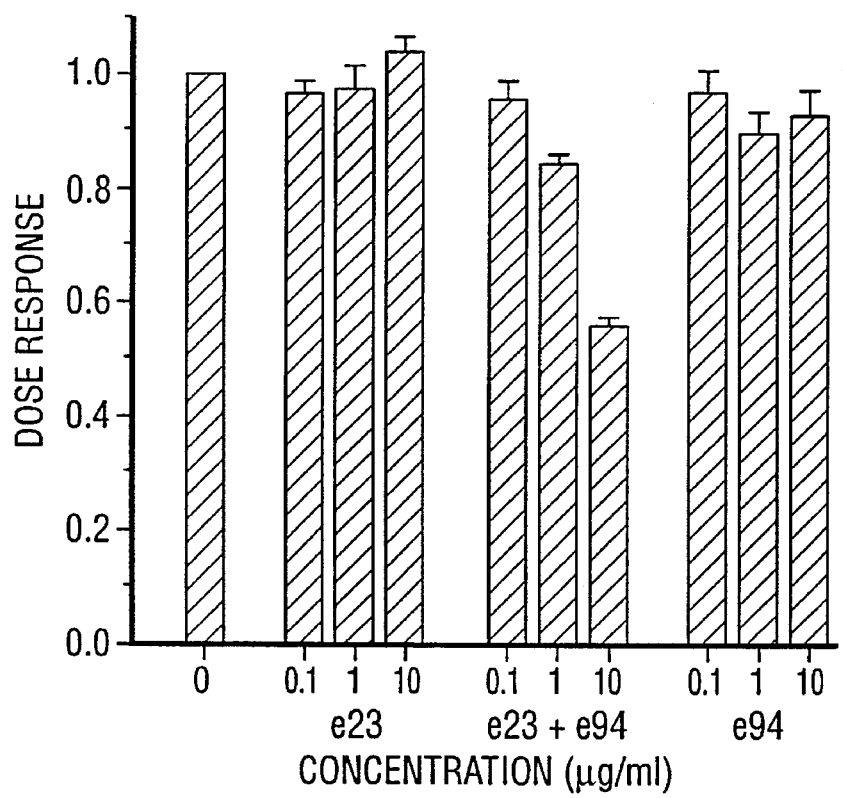

FIG. 6. Effects of e23 and e94 on the growth of human Calu-3 lung adenocarcinoma tumor cells in a monolayer MTT growth assay. A single cell suspension of 10,000 cells/well was plated in a chemically defined medium consisting of RPMI-1640 supplemented with insulin (5 µg/ml), human transferrin (10 µg/ml), 17-β-estradiol (10 nM), sodium selenite (5 nM), and 10 mM Hepes. PBS, e23, e94 or a combination of e21 and e23 at the indicated concentration were then added. The plates were grown at 37° C. in a 5% $CO_2$ humidified atmosphere. After 7 days, 50 µl of 3-(4,5-dimethylthiazol-2-yl)-2,5-diphenyl tetrazolium bromide (0.1 mg) were added and allowed to incubate for 4 hours at 37° C. 90% of the media was then removed and the crystals solubilized in 0.175 ml DMSO. Optical densities were measured at 540 nm in a Molecular Devices Vmax kinetic microplate reader. Results are the average of eight wells with standard deviations noted. Under the conditions used, the cell number is directly proportional to MTT reduction.

FIG. 7. [SEQ ID NO. 1] The cDNA sequence for the *single chain anti-erbB-2 antibody, containing heavy and light variable domains derived from e23 (e23(Fv)).

FIG. 8. [SEQ ID NO. 2] The cDNA sequence for the *single chain anti-erbB-2 antibody, containing heavy and light variable domains derived from e21 (e21(Fv)).

Figure 9:
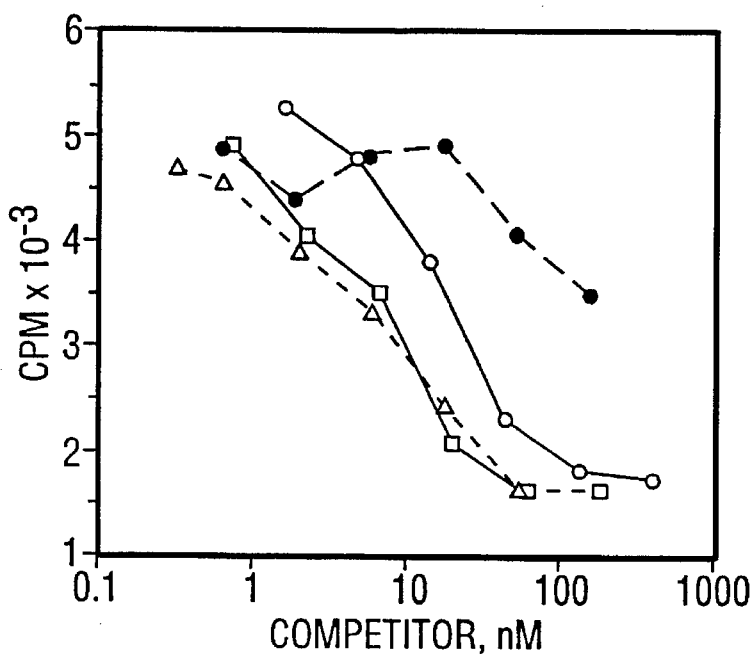

FIG. 9. Depicts the binding of SC(Fv) and immunotoxin to erbB-2. The ability of purified e23(Fv)(O) and e23(Fv)PE38KDEL (●) to inhibit the binding of $I^{125}$-labeled e23 Fab was measured using cells overexpressing erbB-2 N87 as the binding target. Also shown are e23 Fab (□) and intact antibody e23 (△).

Figure 10:
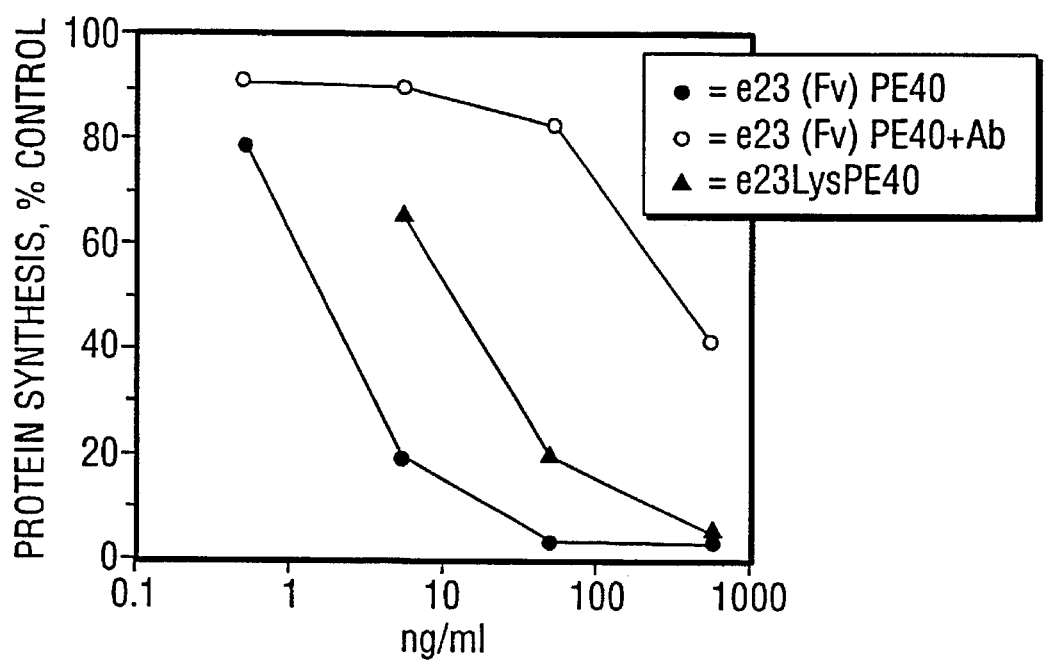

FIG. 10. Depicts the cytotoxicity of e23(Fv)Pe40 on BT474 cells as shown by inhibition of protein synthesis. Results are shown as percentage of control cells to which no toxin was added, ●, e23(Fv) PE40 alone; o, e23(Fv)PE40 plus e23 (20 µg/ml); ▲, e23-LysPE40.

Figure 11:
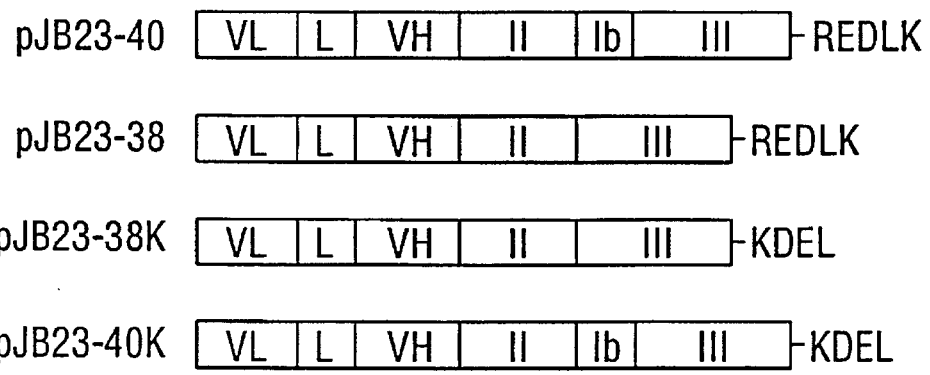

FIG. 11. Depicts schematically the e23(Fv)PE40 derivatives which were synthesized. VH, variable region of heavy chain; VL, variable region of light chain; L, linker; II, domain II of PE; Ib, domain Ib of PE; III, domain III of PE. Carboxyl-terminal amino acid sequences are shown in single letter code.

Figure 12:
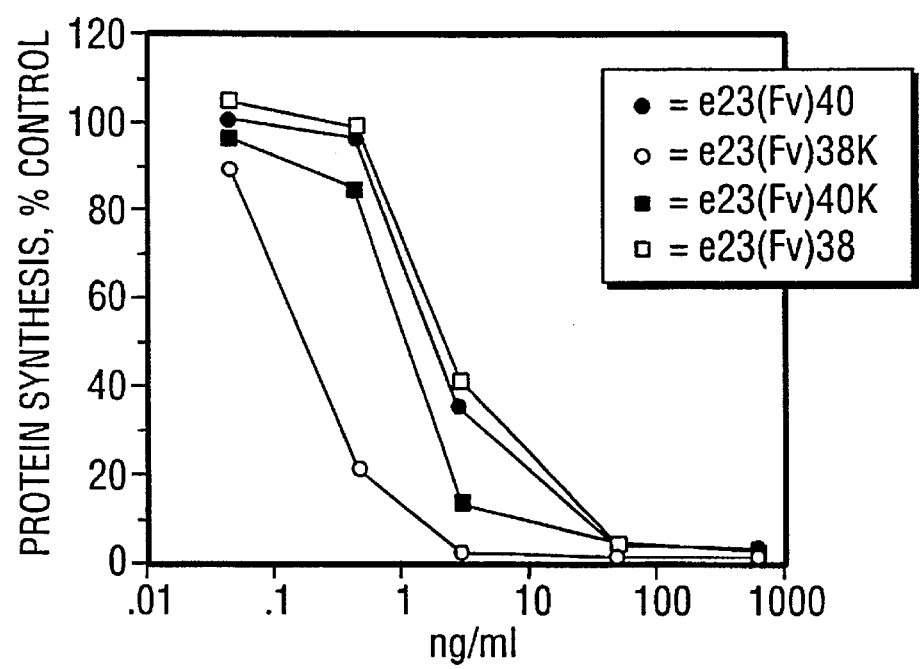

FIG. 12. Depicts the comparative cytotoxic activities of various e23(Fv)PE40 derivatives on BT474 cells, ●, e23(Fv)PE40; o, e23(Fv)PE38KDEL; e23(Fv)PE40KDEL; □, e23 (Fv)PE38.

Figure 13:
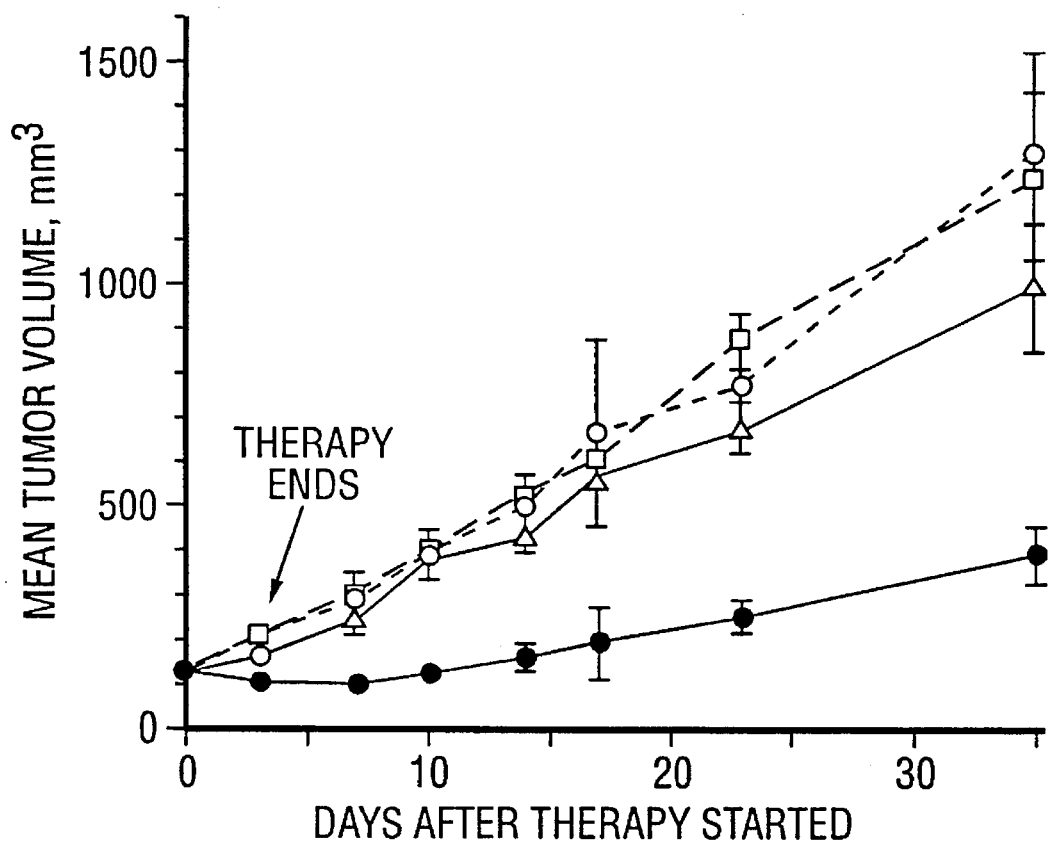

FIG. 13. Depicts results of therapy of tumors formed in mice by human gastric cell line N87. Tumors were established by injection of $5\times10^6$ N87 cells subcutaneously on the backs of BNX mice. Therapy was initiated 7 days following injection of cells. Treatments were twice daily injections in the tail vein with 2 µg of e23(Fv)PE38KDEL(●), LysPE38KDEL(o), or e23Fab(△) or with phosphate-buffered saline (□). Measurements were conducted externally with calipers.

DETAILED DESCRIPTION OF THE INVENTION

One object of the invention is to provide novel antibodies capable of specifically binding to the erbB-2 protein, and do not substantially bind to human cells which antibodies may be used for the treatment and/or prevention of erbB-2 expressing tumors, or the detection of erbB-2 expressing tumor cells. In particular, the invention is directed to novel murine monoclonal antibodies capable of specifically binding to erbB-2 protein, gp185$^{erbB-2}$, and single chain antibodies containing variable heavy and light domains derived therefrom. More particularly, the invention is directed to novel monoclonal antibodies designated e23, e21 and e94, and single chain antibodies containing variable heavy and light domains derived therefrom, the synthesis of which is set forth infra.[1]

[1] The e21, e23 and e94 antibodies disclosed herein are respectively identical to Ab#21, Ab#23 and Ab#94 disclosed in the parent applications 07/906,555 and 07/772,270. The nomenclature has been changed so that it is consistent with current literature relations to these antibodies.

Another object of the invention is to provide novel combinations of at least two different antibodies capable of binding to the erbB-2 receptor, wherein the antibodies are separately capable of treating and/or preventing the expression of erbB-2 expressing tumor cells. Preferably, these antibody combinations will exhibit greater (synergistic) cytotoxic activity than would be expected for the sum of the individual antibodies if administered separately at the same overall antibody concentration. The present inventors have unexpectedly discovered that the combination of at least two different anti-erbB-2 antibodies may provide for greater cytotoxicity than would be expected for the same overall concentration of each individual antibody if administered separately.

Preferably, at least two of these antibodies will recognize distinct erbB-2 epitopes and will not cross react with the other. However, the present inventors do not want to be restricted thereby, but rather intend to embrace any combination of anti-erbB-2 antibodies, which provides for synergistic cytotoxic activity. In the preferred embodiment, the antibody combinations will comprise e23 and e21 or e23 and e94.

The erbB-2 antibodies which are suitable for use in such combinations may include monoclonal antibodies capable of binding to erbB-2, recombinant erbB-2 antibodies, chimeric erbB-2 antibodies which comprise constant and variable domains derived from different species, such as murine-human chimeric antibodies (wherein the constant domain is human and the variable domain is of murine origin), humanized forms of such antibodies, single chain antibodies capable of binding to the erbB-2 protein, and fragments or analogues of erbB-2 monoclonal antibodies which are capable of binding to the erbB-2 protein, and which antibody combinations exhibit synergistic cytotoxic activity. Additionally, the invention further embraces the use of bispecific antibodies, in particular bispecific antibodies comprising the fusion of two different erbB-2 binding single chain antibodies, preferably each of such single chain antibodies binding to a distinct erbB-2 epitope.

Such erbB-2 antibodies will be made by conventional methods. For example, erbB-2 monoclonal antibodies may be obtained through genetic recombination or via Kohler-Milstein fusion techniques. Methods for making antibodies by recombinant methods are well known in the art and include, e.g., the methods disclosed by Cabilly et al, U.S. Pat. No. 4,816,567 and Boss et al, U.S. Pat. No. 4,816,347.

Hybridoma cell lines which secrete e23 and e21 were both deposited on Apr. 4, 1994 at the American Type Tissue Collection in Rockville, Md. and been respectively designated ATCC Accession Nos. HB11601 and HB11602. Both of these cell lines were deposited in accordance with the Budapest Treaty. All restrictions as to the availability of these cell lines will be irrevocably removed upon issuance of a patent in this application, or any other application which claims benefit to this application or to which this application claims benefit.

Methods for making single chain antibodies having binding specificity to a predetermined antigen are also known and are disclosed, e.g., in U.S. Pat. No. 4,946,778 to Ladner et al, U.S. Pat. No. 4,704,692 to Ladner, and U.S. Pat. No. 4,939,666 to Hardman. Methods for making single chain antibody fusions are disclosed in Chaudhary et al, *Proc. Nat'l. Acad, Sci.,* (1990), 87, 1066–1070.

As discussed supra, the claimed antibody combinations will provide for the treatment and/or prevention of cancers associated by the overexpression of erbB-2 protein. Preferably, the first and second antibodies will be combined such that the resultant ratio of the first to second antibody is effective for decreasing the expression of the erbB-2 protein, since the expression of this protein is implicated in the prognosis of some cancer types. More preferably, the combination of antibodies will provide for enhanced decrease of erbB-2 protein expression relative to the same concentration of the individual antibodies contained therein. A convenient method for assaying the expression of the erbB-2 gene product comprises studying the effect of antibody binding on erbB-2 protein turnover (the results of which are depicted in FIG. 4). However, any method which provides for the quantitation of erbB-2 expression, e.g., Northern analysis, should be applicable. The decrease in the expression of the erbB-2 gene product is believed to result from the administered antibody or antibodies decreasing the half-life of the erbB-2 protein in the cell.

Antibody combinations which exhibit synergistic activity will be selected on the basis of those antibodies which in combination reduce erbB-2 receptor expression greater than any of the individual antibodies at the same overall antibody concentration. The relative ratios of the respective antibodies which are contained in the subject antibody combinations will vary dependent upon the number of different antibodies, their epitopic specificity, isotype, binding affinity, etc. An example of a suitable ratio of the first and second antibodies (assuming that the combination comprises two different erbB-2 antibodies) comprises a ratio of from about 1:2 to about 2:1. Preferably, the ratio will be about 1:1.

However, the invention is not restricted to any particular antibody ratio, but rather embraces any combination of at least two different erbB-2 specific antibodies which provide for reduced erbB-2 receptor expression, and preferably provides for a synergistic reduction in erbB-2 receptor expression and inhibition of erbB-2 expressing tumor cells as a result of the selected combination of erbB-2 antibodies.

As discussed supra, another object of the invention is to provide novel methods and compositions for the treatment and/or prevention of erbB-2 expressing tumor cells comprising the administration of a therapeutically effective amount of at least one of the subject novel erbB-2 monoclonal antibodies or single chain antibodies of the invention, namely e21, e23, e94 (the preparation of which is disclosed in the following examples), single chain antibodies containing variable heavy and light domains derived therein, and antibodies having the identifying characteristics thereof. Identifying characteristics are intended to include those properties which affect the immuno-binding of the particular anti-erbB-2 antibody, in particular epitopic specificity.

These antibodies may be administered by themselves, or these antibodies may be attached to cytotoxic moieties, which include e.g., radioactive materials, anti-cancer drugs (e.g., daunomyocin, adriamycin, chlorambucil), anti-metabolites (e.g., methotrexate), inhibitors of protein synthesis (e.g., diptheria toxin, Pseudomonas exotoxin, ricin, abrin, etc.), and agents which bind DNA (such as alkylating agents). In a preferred embodiment, the subject erbB-2 specific antibodies will be attached to a Pseudomonas exotoxin A variant which lacks the N-terminal domain (domain I) which is responsible for the binding of the exotoxin to its corresponding cell receptor. A particularly preferred Pseudomonas exotoxin A variant is PE40, the sequence of which is disclosed e.g., in Hwang et al, *Cell,* (1987), 48, 129–136 and Siegall et al, *J. Biol. Chem.,* (1989), 264, 14256–14261 which references are incorporated by reference herein. Thereby, the subject anti-erbB-2 antibody Pseudomonas A exotoxin conjugates only comprise the binding function of the erbB-2 antibodies, and do not exhibit non-specific binding attributable to the exotoxin. In a more preferred embodiment, the Pseudomonas exotoxin A variants which are attached to the subject erbB-2 antibodies will also comprise a deletion of amino acids 365–380 (which eliminates a disulfide bond) and/or the deletion of the five C-terminal amino acids and the substitution of a tetrapeptide, KDEL, therefor. Such Pseudomonas exotoxin A variants are known in the literature, and are described e.g., in Brinkmann et al, *Proc. Nat'l. Acad. Sci.,* (1991), 88, 8616–8620; Hwang et al, *Cell,* (1987), 48, 129–136; Seetharam et al, *J. Biol. Chem,* (1991), 266, 17376–17381; and Siegall et al, *J. Biol. Chem.,* (1989), 264, 14256–14261, which references are incorporated by reference in their entirety.

Preferably, the antibody which is administered will comprise e23, its corresponding single chain antibodies, humanized antibodies derived from e23, chimeric antibodies, (containing the variable sequences therefrom and human constant domain sequences) or therapeutic diagnostic conjugates thereof since this antibody has been found to bind to erbB-2 expressing tumor cells with high affinity, and to not substantially bind to normal human tissues. This is advantageous both for diagnostic and therapeutic applications since it avoids false positives (if the antibodies are utilized diagnostically to assay for cancers associated with overexpression of $gp185^{erbB-2}$) and also avoids cytotoxicity to normal human cells when the antibodies are used therapeutically since this antibody does not substantially bind to normal human cells.

Avidin-biotin immunoperoxidase binding assays with e23 and a number of different normal tissues have established that e23 only reacts with the membrane of simple, stratified, and squamous epithelial cells in normal human tissues. (These assays and the results thereof are described infra). This narrow range of reactivity with normal human cells is unexpected given that the erbB-2 receptor is known to be comprised on a large number of normal human tissues. It is known e.g., that erbB-2 is expressed throughout the intestinal, respiratory, urinary and reproductive tracts, as well as the skin of fetal and adult specimens (Press et al, *Oncogene,* (1990), 5, 953–962). More particularly, the erbB-2 receptor is expressed in normal uterine endometrial tissues (Brumm et al, *Virhous Archiv. A Pathol. Anat.,* (1990), 417,477–484; normal breast tissues (Tsutsumi et al, *Hum Pathol,* (1990), 21, 750–758; Potter et al, *Histopathology,* (1989), 15,351–362) and kidney tissues (Potter et al, *Int. J. Cancer,* (1989), 44,969–974).

It has been suggested in the literature that the erbB-2 receptor may be expressed in a different form on the surface of cancer tissues than normal cells. Accordingly, the low reactivity observed with e23 and normal human tissues may be attributable to it binding an erbB-2 epitope which is selectively expressed on erbB-2 receptor expressing tumor cells.

The subject antibodies or antibody combinations will be administered to cancer patients having cancers associated by overexpression of erbB-2 protein by standard routes of administration, e.g., intraperitoneally via intravenous, or intramuscular routes. The effective dosage of the antibodies will vary dependent e.g., upon the particular antibody or antibody combination which is administered, whether or not the antibody or antibodies are conjugated to a therapeutic effective moiety, the particular therapeutic moiety (e.g., a toxin, radioactive moiety, or alkylating agent), and the condition of the patient being treated.

Preferably, the effective concentration at the target tumor site will be at least 1 μg/ml, and will not exceed 10 μg/ml. In general, in order to achieve the desired concentration of the antibody or antibodies at the tumor site the antibody or antibody combination will be administered at a dose ranging from about 0.1 mg/kg to about 10 mg/kg of body weight.

As noted supra, the subject anti-erbB-2 antibodies may be administered in unmodified form, or one or more of the subject antibodies may be administered on the form of immunotoxins. Methods for the construction of immunotoxins are well known in the art. Generally, such techniques involve direct covalent attachment or the complexation of an antibody to a therapeutic moiety, e.g., an anti-cancer pharmaceutical agent, a cytotoxin, a radioactive compound (e.g., isotopes of boron and rhenium); agents which bind DNA, such as alkylating agents, anti-cancer compounds (e.g., daunomycin, adriamycin, chlorambucil); anti-metabolites (e.g., methotrexate); and inhibitors of protein synthesis (e.g., diphtheria A chain, nonbinding active fragments of diphtheria toxin, exotoxin A chain (from *Pseudomonas aueroginosa,* ricin A chain, abrin A chain, modaccin A chain, alpha-sarcin, *Aleurites fordii* proteins, dianthin proteins, *Phytolacca americana* proteins (PAPI, PAPII, and PAP-S), Momordica charantia inhibitor, curcin, crotin, Sapaonaria officinalis inhibitor, gelonin, mitogellin, restrictocoin, phenomycin and enomycin. Alternatively, the subject antibodies may be attached to a desired therapeutic-moiety using known bifunctional protein coupling agents. Examples of such coupling reagents are SPDP, IT, bifunctional derivatives of imidoesters such as dimethyl adipimidate HCl, active esters such as disuccinimidyl suberate, glutaraldehyde, bis-azido compounds, bis-diazonium compounds and diisocyanates of bis-active fluorine compounds. Preferably, the attachment of the antibody to a therapeutic moiety will be effected in a manner which minimizes loss of antibody binding function.

If the administered erbB-2 antibody or antibodies comprises a single chain antibody, the antibody will preferably be attached to a therapeutic moiety since such antibodies lack the Fc effector portion of the antibody. In such cases, attachment will be effected by expressing a DNA fusion of the subject single chain erbB-2 antibody coding sequences and a DNA sequence which encodes for a polypeptide exhibiting therapeutic activity. Generally, such therapeutic moieties will comprise polypeptide toxins or active variants thereof. The construction of such single chain antibody-toxin fusions is exemplified infra in the examples. Moreover, methods for expressing single chain antibody-therapeutic moiety DNA fusions are disclosed in U.S. Pat. No. 5,132, 405 by Huston et al. In the preferred embodiment the subject anti-erbB-2 single chain antibodies will be fused to variants of the Pseudornonas exotoxin A which lack the N-terminal binding domain, and which may be further modified to eliminate disulfide bond formation (e.g., by deletion of amino acids 365–380) and/or which comprise deletions of the five C-terminal amino acids and the substitution of a tetrapeptide, KDEL, therefor. Such Pseudomonas exotoxin A variants are known in the literature as discussed supra.

The administration of the subject anti-erbB-2 antibodies in combination with a discrete therapeutic moiety, e.g., a cis-platinum type compound is further envisioned since it has been reported that a monoclonal antibody directed to erbB-2 enhances the cytotoxicity of cis-diamminedichloroplatinum against human breast and ovarian tumor cell lines. (Hancock et al, *Cancer Res.,* (1991 ), 51, 4575–4580).

For parenteral administration the subject antibodies or antibody combinations may be formulated in a unit dosage injectable form (solution, suspension, emulsion) in association with a pharmaceutically acceptable parenteral vehicle. Examples of such vehicles are water, saline, Ringer's solution, dextrose solution, and 5% human serum albumin.

Nonaqueous vehicles such as mixed oils and ethyl oleate may also be used. Liposomes may also be used as carriers. The vehicles may contain minor amounts of additives that enhance isotonicity and chemical stability, e.g., buffers and preservatives. The subject antibodies and antibody combinations will typically be formulated in such vehicles at concentrations of about 1 µg/1 ml to 10 µgl/ml.

As noted, a preferred embodiment of the invention will comprise administration of a therapeutically effective amount of a combination of at least two different anti-erbB-2 antibodies. The present inventors have found that combinations of anti-erbB-2 antibodies may provide for synergistic cytotoxic activity. In the most preferred embodiments, the combination of antibodies will comprise e21 and e23, or e23 and e94. However, the invention is not restricted to such combinations, but rather embraces any combination of erbB-2 antibodies which provides for enhanced cytotoxic activity then the equivalent overall concentration of the individual antibodies contained in the combination.

Preferably, the different antibodies will bind to different erbB-2 epitopes and will not cross-react with each other. Although the present inventors do not want to be limited to any theoretical reasoning, a possible mechanism by which the down regulation and protection and/or killing of human cancer cells overexpressing erbB-2 is achieved by the present invention is that the antibodies act by constraining the erbB-2 gene product, $gp185^{erbB-2}$ into an activated conformation thus mimicking an agonist ligand.

The results disclosed herein demonstrate that a combination of erbB-2 receptor binding antibodies leads to different and more potent anti-tumor activities than single antibodies. More specifically, the results indicate that combination antibody therapy is a useful strategy for treatment of malignancies associated by overexpression of $185^{erbB-2}$. This approach may be particularly important in the treatment of cancers such as gastric cancer which respond poorly to currently available chemotherapies.

As discussed supra, another object of the invention relates to the use of the novel erbB-2 monoclonal and single chain antibodies of the invention as diagnostic agents for assaying for the presence of $gp185^{erbB-2}$ overexpressing tumor cells in analytes, e.g., blood serum and tumor biopsies.

The use of anti-erbB-2 specific monoclonal antibodies as diagnostic agents for detecting erbB-2 cancer cells is known in the art, as disclosed e.g. in U.S. Pat. No. 4,938,948 to Ring et al., and WO 89/06692 by Hudziak et al, published on Jul. 27, 1989. The $gp185^{erbB-2}$ binding antibodies of the invention should be particularly suitable as diagnostic agents given their high binding affinity to the erbB-2 receptor. It is especially envisioned that e23 and single chain antibodies derived therefrom should be advantageous diagnostic agents, given the narrow range of binding of this antibody to normal human tissues. Thus, the use of e23 and its corresponding single chain antibody should reduce the likelihood of false positive binding results. This is a particular concern with assays which measure erbB-2 receptor expression since this protein is known to be comprised in detectable amounts on a large number of different normal human tissues.

Essentially, a sample suspected of containing erbB-2 expressing cancer cells will be incubated with the subject antibody or antibodies for a sufficient time to permit immune reactions to occur. Those skilled in the art will recognize that there are many variations in these basic procedures. These variations include, for example, RIA, ELISA, precipitation, agglutination, complement fixation and immunofluorescence. Preferably, the subject antibodies will be labelled to permit the detection of antibody-erbB-2 immunocomplexes.

The labels that are used in making labeled versions of the antibodies include moieties that may be detected directly, such as radiolabels and fluorochromes, as well as moieties, such as enzymes, that must be reacted or derivatized to be detected. The radiolabel can be detected by any of the currently available counting procedures. The preferred isotope labels are $^{99}Tc$, $^{14}C$, $^{131}I$, $^{125}I$, $^{3}H$, $^{32}P$ and $^{35}S$. The enzyme label can be detected by any of the currently utilized calorimetric, spectrophotometric, fluorospectrophotometric or gasometric techniques. The enzyme is combined with the antibody with bridging molecules such as carbodiimides, periodate, diisocyanates, glutaraldehyde and the like. Many enzymes which can be used in these procedures are known and can be utilized. Examples are perioxidase, alkaline phosphatase, β-glucuronidase, β-D-glucosidase, urease, glucose oxidase plus peroxidase, galactose oxidase plus peroxidase and acid phosphatase. Fluorescent materials which may be used include, for example, fluorescein and its derivatives, rhodamine and its derivatives, auramine, dansyl, umbelliferone, luciferia, 2,3-dihydrophthalazinediones, horseradish peroxidase, alkaline phosphatase, lysozyme, and glucose-6-phosphate dehydrogenase. The antibodies may be tagged with such labels by known methods. For instance, coupling agents such as aldehydes, carbodiimides, dimaleimide, imidates, succinimides, bis-diazotized benzadine and the like may be used to tag the antibodies with the above-described fluorescent, chemiluminescent, and enzyme labels. Various labeling techniques are described in Morrison, *Methods in Enzymology*, (1974), 32B, 103; Syvanen et al., *J. Biol. Chem.*, (1973), 284, 3762; and Bolton and Hunter, *Biochem J.*, (1973), 133, 529.

The antibodies and labeled antibodies may be used in a variety of immunoimaging or immunoassay procedures to detect the presence of cancer in a patient or monitor the status of such cancer in a patient already diagnosed to have it. When used to monitor the status of a cancer, a quantitative immunoassay procedure must be used. If such monitoring assays are carried out periodically and the results compared, a determination may be made regarding whether the patient's tumor burden has increased or decreased. Common assay techniques that may be used include direct and indirect assays. If the sample includes cancer cells, the labeled antibody will bind to those cells. After washing the tissue or cells to remove unbound labeled antibody, the tissue sample is read for the presence of labeled immune complexes. In indirect assays the tissue or cell sample is incubated with unlabeled monoclonal antibody. The sample is then treated with a labeled antibody against the monoclonal antibody (e.g., a labeled antimurine antibody), washed, and read for the presence of ternary complexes.

For diagnostic use the antibodies will typically be distributed in kit form. These kits will typically comprise: the antibody in labeled or unlabeled form in suitable containers, reagents for the incubations for an indirect assay, and substrates or derivatizing agents depending on the nature of the label. $gp185^{erbB-2}$ controls and instructions may also be included.

The following examples are offered to more fully illustrate the invention, but are not to be construed as limiting the scope thereof.

The following materials and methods were used in Examples 1–5.

MATERIALS AND METHODS

Monoclonal Antibodies. Mice were immunized using a membrane preparation of N/erbB-2 cells (NIH/3T3 cells engineered to overexpress the human erbB-2 protein). Following tests of polyclonal antibody response using immunoprecipitation, three fusions were conducted using the myeloma cells line Ag8.653 and standard techniques. These fusions produced approximately 1500 hybridoma clones which were each screened using enzyme-linked immunosorbent assay. Membranes isolated from N/erbB-2 cells were bound to polystyrene plates, and culture medium was added to allow antibody-antigen interaction. Immunoglobulin binding was detected using a biotinylated goat antimouse antibody, streptavidin horseradish peroxidase, and o-phenylenediamine hydrochloride. Positive reacting hybridomas were picked and counter-screened using membranes from wild-type NIH/3T3 membranes. The molecular specificity was confirmed by immunoprecipitation analysis. Five hybridomas were picked with anti-erbB- 2-specific reactivity and cloned by limiting dilution; three of these were designated as e21, e23 and e94. Ascites was prepared by administering injections of $10^6$ hybridoma cells to pristane-primed mice. Antibodies were isolated in large amounts from ascites fluid and purified by high-performance liquid chromatography with a Gammabind Ultra column (Genex, Gaithersburg, Md.). SDS-PAGE[2] was run under nonreducing conditions using Coomassie blue staining with a single band at $M_r$ 180,000 observed, indicating a >98% purified preparation. From 1 ml of ascites approximately 8–15 mg of antibody were routinely purified.

[2]The abbreviations used are" SDS-PAGE, sodium dodecyl sulfate-polyacrylamide gel electrophoresis; PBS, phosphate-buffered saline; MTT, 3-(4-5-dimethylthiazol-2-yl)-2,5-diphenyl tetrazolium bromide; cDNA, complementary DNA.

Cells Lines and Tissue Culture.

The human gastric tumor cell line used in these studies, N87, has been previously described in the literature and was routinely subcultured in RPMI 1640 supplemented with 10% fetal bovine serum. The cell lines SK-Br-3, MDA-MB-468, and MDA-MB-231 (breast) and SK-OV-3 (ovarian) were routinely subcultured in improved minimal essential medium (IMEM) supplemented with 5% fetal bovine serum. Cultures were maintained in humidified incubators at 37° C. in an atmosphere of 5% $CO_2$ and 95% air. Cells were tested for Mycoplasma using a ribosomal RNA hybridization method (GenProbe, San Diego, Calif.).

Growth Inhibition Assays.

A single cell suspension of 10,000 cells/well was plated in a serum-free defined media of RPMI 1640 containing bovine serum insulin (5/µg/ml final concentration) was then added. The plates were incubated for 5–7 days in a $CO_2$ incubator with humidity at 37° C. Cell viability was monitored by one of two different methods. The first, the MTT assay (Mossman et al, J, Immun. Meth., (1983), 65, 55–63), is based on the ability of live cells to reduce a tetrazolium-based compound, MTT, to a purplish colored formazan product that can be measured spectrophotometrically. After 7 days, 50 µl of MTT reagent (0.1 mg) were added and allowed to incubate for 4 h at 37° C. Ninety % of the media was then removed, and the crystals were solubilized in 0.175 ml dimethyl sulfoxide with absorbance measured at 540 nm in a Molecular Devices Vmax kinetic microplate reader. The second method involves the cell number measurement in monolayer cultures by crystal violet staining (Sibler et al, Anal. Biochem., (1989), 182, 16–18). Cells were plated as above and after 7 days cells were fixed by the addition of 20 µl of a 11% glutaraldehyde solution. After being shaken on a Bellco Orbital Shaker for 15 min the plates were washed three times with deionized water. Plates were then air-dried and stained by the addition of 100 µl of a 0.1% solution of crystal violet dissolved in 200 mM borate, pH 6.0. After being shaken for 20 min at room temperature, excess dye was removed by extensive washing with deionized water, and the plates were air-dried prior to solubilization in 100 µl of 10% acetic acid. Absorbance was measured at 590 nm in the microplate reader.

Antibody Specificity.

Subconfluent SK-Br-3 monolayers were metabolically labeled with $[1^{35}S]Cys$ (specific activity, 1000 Ci/mmol). Total cell proteins were immunoprecipitated with 10 µl of the indicated antibodies. The immune complexes were recovered by protein G-Agarose (Genex) and analyzed by SDS-PAGE on an 8–16% Tris-glycine gel. The gel was exposed to film at −70° C. overnight with an intensifying screen.

Western Blots.

Cells or tumors were lysed in sample buffer which contained 0.125 M Tris-HCl, 4% SDS, 0.002% bromophenol blue, and 15% glycerol. Five % α-mercaptoethanol was added after the protein concentration was determined. Samples (10 µg total protein) were boiled for 3 min, fractionated by SDS-PAGE on 8–16% Tris-Glycine gel (Novex, Encinitas, Calif.), and transferred to nitrocellulose. Detection of gp185$^{erbB-2}$ was performed with a monoclonal antibody (E2-4001; Molecular Oncology, Inc. to the COOH-terminal portion of the protein.

Southern Blots.

DNA was extracted from cell lines and human placenta tissue using guanidine thiocyanate and cesium gradient centrifugation. DNA (15 µg) was cleaved with restriction enzyme HindIII, separated by electrophoresis on a 1% agarose gel, transferred to nitrocellulose, and probed with a radioactive erbB-2 cDNA prove as previously described (King et al, Cancer Res., (1989), 49, 4185–4191). The cDNA probe corresponds to the entire erbB-2 protein coding region.

In Vivo Antitumor Assay.

Tumor cells ($5 \times 10^6$/mouse) were injected s.c. into the flanks of BNX (beige, nude, xid) mice. The day after cell inoculation treatment was begun which consisted of four trial groups (3 mice/group), each given 0.2-ml i.p. treatment injections twice a week. Tumor growth was monitored at least once a week and reported as an average relative tumor volume. The effect of treatment after the formation of small tumors was also carried out. Cells were injected using the same treatment protocol as above except that the treatment was begun 4 days after cell injection instead of 1 day after. Animal care was in accordance with institutional guidelines. Statistical analysis was carried out using a SAS Computer Package (SAS Institute, Cary, N.C.).

gp185$^{erbB-2}$ Stability Assay.

Subconfluent N87 cell monolayers were pulse-labeled 1 h with 20 µCi[$^{35}$S]cysteine and then chased with 5 mM Cys in the presence of antibody for 24 h. Total cellular protein was immunoprecipitated as described above using a monoclonal antibody directed against the COOH terminus of gp185$^{erbB-2}$ coupled to Sepharose and analyzed by SDS-PAGE. The gel was exposed to film at −70° C. overnight with an intensifying screen.

Tyrosine Phosphorylation.

Cells were plated as in the protein stability assay. After 1 h, cells were processed, and proteins were extracted in sample buffer for electrophoresis as the antibody specificity experiment. Following electrophoresis in the proteins were electroblotted onto nitrocellulose paper and incubated with anti-phosphyotyrosine IgG (monoclonal; Upstate Biotechnology, Inc.) and immunodetected using $^{125}$I-protein A. The gel was exposed to film at −70° C. overnight with an intensifying screen.

EXAMPLE 1

Preparation of Antibodies and Immunological Characterization Thereof

The procedure described in the Materials and Methods Supra was used to produce three monoclonal antibodies which were designated e21; e23; and e94.

In particular, monoclonal antibodies directed against the extracellular domain of $gp185^{erbB-2}$ were tested for specific reaction to N/erbB-2 cell membranes in an ELISA assay. Two of these designated e21 and e23 after screening in growth assays exhibited the highest biological activity and were subjected to further testing.

Both antibodies specifically immunoprecipitated a single $^{35}$S-labeled protein of MW 185,000 from SK-Br-3 cells, a breast cancer cell line which overexpresses $gp185^{erbB-2}$ protein, (Kraus et al, *EMBO J.*, (1987), 6, 605) as shown in FIG. 1A. No immunoprecipitation was detected in cells which do not overexpress the $gp185^{erbB-2}$ protein (e.g., MDA-MB-468, data not shown).

Because the erbB-2 oncogene is overexpressed frequently in at least 20% of stomach cancer, which have a poor clinical course, the effect of these antibodies on cell proliferation was studied on a gastric cell line, N87, which overexpresses $gp185^{erbB-2}$ at levels commensurate with SK-Br-3. An immunoblot of the N87 cell line and a nude mouse tumor xenograft from N87 is shown in FIG. 1B compared to the breast cell lines SK-Br-3 (high level of $gp185^{erbB-2}$ overexpression) and MDA-MB-231 (low level of $gp185^{erbB-2}$ overexpression). The levels of erbB-2 gene amplification in N87 as shown in FIG. 1C surpassed those found in the well characterized SK-Br-3 and SK-OV-3 cell lines (Kraus et al, *EMBO J.*, (1987), 6, 605).

EXAMPLE 2

Effect of Antibodies on Tumor Growth In Vitro

A dose response analysis of the effects of the antibodies on N87 cell proliferation is shown in FIG. 2. Antibodies e21 or e23 administered individually had no effect on the monolayer growth of cells up to a concentration of 10/μg /ml (6 μM). Administration of a 1:1 combination of e21 and e23, however, markedly affected cell proliferation at doses as low as 1 μg/ml. Fab fragments prepared from both antibodies also had no effect on cell growth alone or in combination (data not shown). In analogous experiments with three other gastric cell lines displaying little or no overexpression by immunoblot analysis, no inhibition of growth even at the highest dose was observed with the antibody combination or the antibodies alone.

EXAMPLE 3

Preventive Combination Antibody Therapy

The efficacy of combination antibody therapy was tested on the growth of N87 tumor xenografts. One inoculation of five million N87 cells were injected subcutaneously into nude mice produced rapidly growing tumors with a short latency. Tumor growth at the injection site was easily quantitated. As shown in FIG. 3A, the N87 cells did not form tumors in the animals treated twice a week for three weeks with a total of 200 μg of antibodies per injection with the combination of e21 and e23. In sharp contrast they were potently tumorigenic in animals treated with the single antibodies or PBS and the tumor grew to over 1 cm³ in tumor volume over the period measured. In contrast to in vitro experiments, each monoclonal antibody alone may have limited activity to partially restrict the rate of tumor growth. However, the activity exhibited by the combination far exceeded the cumulative effect expected from the combination.

To determine if the combined therapy with e21 and e23 was able to eradicate established tumors, an experiment was performed in which tumors were allowed to grow to measurable sizes prior to antibody treatment. The results are illustrated in FIG. 3B. In animal groups randomized so that the starting size of the tumors was near the same volume (100 mm³), the tumors continued to grow when the animals were given single antibody treatment of e21 or e23 (200 μg/injection, 2 injection/week, 3 weeks, 6 mice). In contrast, in the animals given two antibody combination treatment of e21 and e23, results shown are the average of 6 animals, tumors completely regressed after 11 days (4 treatments of 200 μg of total antibody). This is the first reported observation of tumor xenograft regression induced by a combination of different anti-erbB-2 monoclonal antibodies. Previous studies have shown that two anti-neu antibodies can inhibit the growth of tumors by murine cells transformed by the mutationally activated neu oncogene (Drebin et al, *Oncogene*, (1988), 2, 273). The activation of the murine neu oncogene is accomplished by point mutation as evidenced by qualitative interference in the structure and function of the neu gene, whereas the human erbB-2 oncogene is activated by overexpression of erbB-2, a quantitative interference of the apparently normal protein which results in tumor formation.

Since the mechanisms for tumor growth are so different between murine and human, it was unexpected that similar mechanisms of neutralization of the genes involved would be effective. This effect is also seen with the inhibition of leukemic tumor cell growth using anti-transferrin monoclonal antibodies (White et al, *Cancer Res.*, (1990), 50, 6295).

EXAMPLE 4

Antiproliferative Effects of Antibody Combination

To investigate the molecular basis for the antiproliferative effects of e21 and e23, we measured the rate of $gp185^{erbB-2}$ turnover in the presence or absence of antibodies. N87 cells were pulse-labeled with $^{35}$S-Cys and then chased for various times in the presence of single antibody or the e21/e23 combination. The results of a 24 h chase are shown in FIG. 4A. The antibody $gp185^{erbB-2}$ combination induced rapid degradation of $gp185^{erbB-2}$ while the individual antibody treatment had little or no effect. Thus, the antiproliferative effect of e21/e23 treatment might likely be explained by their ability to increase the turnover of $gp185^{erbB-2}$.

EXAMPLE 5

Autophosphorylation Activity of Antibody Combination

To test whether the subject antibodies result in increased $gp185^{erbB-2}$ autophosphorylation, anti-phosphotyrosine immunoblots were effected using N87 cells. Cells were plated as described in the Materials and Methods. After 1 h, cells were processed, and proteins were extracted in sample buffer for electrophoresis when evaluating antibody specificity. Following electrophoresis the proteins were electroblotted onto nitrocellulose paper and incubated with anti-phosphyotyrosine IgG (monoclonal; Upstate Biotechnology, Inc.) and immunodetected using $^{125}$I-protein A. The gel was exposed to film at −70° C. overnight with an intensifying screen.

As shown in FIG. 4B, increases in the tyrosine phosphorylation of gp185$^{erbB-2}$ from N87 cells were observed after 15 min and 1 h after the addition of the single antibodies or the antibodies in combination. (The same results were observed at 30 min and 2 h; data not shown). This suggests that activation of tyrosine activity may be necessary but is probably not essential for growth inhibition.

EXAMPLE 6

Combination Antibody Treatment Effect the Growth of Calu-3 Cells

In order to demonstrate that the effect of combination of anti-erbB-2 antibodies e21 and e23 is not limited to effect on the N87 gastric cancer cell line, we investigated the human lung adenocarcinoma cell line Calu-3. This cell line overexpresses the gp185$^{erbB-2}$ protein as determined by immunoblot analysis (data not shown). In experiments very similar to that described above, the combination of e21 and e23 show dramatic inhibition of cell growth as measured in an MTT assay (FIG. 5). In this experiment, a single cell suspension of 10,000 cells/well was plated in a chemically defined media consisting of RPMI-1640 supplemented with insulin, human transferrin, 17-estradiol. sodium selenite, and Hepes buffer. PBS, e21, e23 or a combination of e21 and e23 were then added. The cells were allowed to grow at 37° C. in a 5% CO$_2$ humidified atmosphere. After 7 days, MTT reagent was added and allowed to incubate for 4 hours at 37° C. 90% of the media was then removed and the crystals solubilized in DMSO. Optical densities were measured at 540 nm in a Molecular Devices Vmax kinetic microplate reader. A dose response analysis of the effects of antibody treatment is shown in FIG. 5. These results indicate that combination antibody therapy is not limited in effectiveness to N87 cells or gastric cancer cells. It also indicates that combination antibody therapy may have effectiveness in the treatment of adenocarcinoma of the lung.

EXAMPLE 7

Effectiveness of other Combinations of Antibodies in Inhibiting Cell Growth

In order to determine if e21 and e23 are unique in their ability to combine to cause growth inhibition, we investigated the combination of e94 and e23 on the growth of Calu-3 cells in vitro. e94 is another monoclonal antibody developed by the present inventors which specifically binds to the erbB-2 protein. An MTT assay of cell growth was conducted as described in EXAMPLE 6. As shown in FIG. 6, the combination of antibodies inhibits cell growth and the individual antibodies do not. This indicates that the ability to combine antibodies to produce a more profound growth inhibition is not limited to a particular antibody combination.

EXAMPLE 8

Generation of a single chain (Fv) from mAb e23

Poly A RNA was extracted from e23 producing hybridoma cells using oligo dT affinity chromatography (In vitrogen). cDNA was prepared using random primer (N$_6$) (Boerhinger Mannheim). The immunoglobulin light and heavy chain clones were isolated using PCR and the primers: light chain, [SEQ ID NO. 3] 5' CAC GTC GAC ATT CAG CTG ACC CAC TCT CCA and [SEQ ID NO. 4] GAT GGA TCC AGT TGG TGC AGC ATC3'; heavy chain [SEQ ID NO. 5] 5'C GGA ATT TCA GGT TCT GCA GIA GTC WGG3' and [SEQ ID NO. 6] 5' AGC GGA TCC AGG GGC CAG TGG ATA GAC3' [G,A,C,T stand for standard nucleotides; I for inosine, W for A or T]. The products of the PCR reaction were cloned into p$^{uc18}$. Linkage into a SC(Fv) was by PCR giving the individual light and heavy cDNA clones and 4 oligonucleotides [SEQ ID NOS. 7–10 ]

5'- cgagatgagtccagctgacccagtctc
5'- gaagatttaccagaaccagaggtagaacctttatttccagcttgga
5'- ctggttctggtaaatcttctgaaggtaaaggtgtgcagctgcaggag
5'- cgagtgcaagcttaggagacggtgaccgt.

The light and heavy chain coding regions were joined by a synthetic linker GSTSGSGKSSEGKG specified by overlapping oligonucleotides as described. The intact scFv coding region was inserted in frame with an E. coli OMPA leader sequence under direction of the lambda P$_L$ promoter. Induction of protein and bacterial lysis and refolding was as previously described (Pantaliano et al, Biochem., (1991), 30, 117–125). scFv was purified as a single peak from CM chromatography and judged to be >70% by SDS gel electrophoresis. This scFv will be referred to herein as e23(Fv).

EXAMPLE 9

Generation of a scFv from mAb e21

Poly A RNA was extracted from e21 producing hybridoma cells using oligo dT affinity chromatography (In vitrogen). cDNA was prepared using random primer (N$_6$) (Boerhinger Mannheim). The immunoglobulin light and heavy chain clones were isolated using PCR and the primers: light chain, [SEQ ID NO. 3] 5' CAC GTC GAC ATT CAG CTG ACC CAC TCT CCA and [SEQ ID NO. 4] GAT GGA TCC AGT TGG TGC AGC ATC3'; heavy chain [SEQ ID NO. 5] 5'C GGA ATT TCA GGT TCT GCA GIA GTC WGG3' and [SEQ ID NO. 6] 5' AGC GGA TCC AGG GGC CAG TGG ATA GAC3'[G,A,C,T stand for standard nucleotides; I for inosine, W for A or T]. The products of the PCR reaction were cloned into pUC18. Linkage into a scFv was by PCR giving the individual light and heavy cDNA clones and 4 oligonucleotides [SEQ ID NOS. 7–10] 5'- cgagatgagtccagctgacccagtctc
5'- gaagatttaccagaaccagaggtagaacctttatttccagcttgga
5'- ctggttctggtaaatcttctgaaggtaaaggtgtgcagctgcaggag
5'- cgagtgcaagcttaggagacggtgaccgt.

The light and heavy chain coding regions were joined by a synthetic linker [SEQ ID NO. 11] GSTSGSGKSSEGKG specified by overlapping oligonucleotides as described. The intact scFv coding region was inserted in frame with an E. coli OMPA leader sequence under direction of the lambda P$_L$ promoter. Induction of protein and bacterial lysis and refolding was as previously described (Pantaliano et al, Biochem., (1991), 30, 117–125). scFv was purified as a single peak from CM chromatography and judged to be >70% by SDS gel electrophoresis. This scFv will be referred to herein as e21(Fv).

EXAMPLE 10

Construction of Single-Chain Immunotoxin with Anti-erbB2 Antibody e23

Single-chain immunotoxins made by the fusion of the antigen-binding region (Fv) and PE40 can retain the binding affinity of the native antibody and are often more active than the respective chemical conjugates (Chaudhary et al, *Proc. Nat'l. Acad. of Sci.*, (1990), 87, 1066–1070; Batra et al, *Mol. Cell Biol.* (1991), 11, 2200–2205.) For this reason, we selected antibody e23 for construction of a first-generation recombinant immunotoxin. The construction of the subject e23 antibody derived single chain antibody immunotoxins is also described in Butra et al, *Proc Natl Acad Sci*, (1992), Vol. 89, pp. 5867–5871, which is incorporated by reference in its entirety herein.

First, an intact sc(Fv) for coding region designated e23(Fv) was generated as described supra. The sequence of the single-chain protein is shown in (FIG. 7). To verify the binding activity of the purified e23(Fv) protein we conducted competition binding using $^{125}$I-labeled e23 Fab (see FIG. 9). The overall structure of our first recombinant immunotoxin is the amino-terminal e23 sc(Fv) domain joined to the translocation (II) and ADP-ribosylating (III) domains of PE. The assembled gene is under control of a bacteriophage T7 promoter. The resulting plasmid, pJB23–40, expresses the variable region of the light chain of e23, a 14-amino acid linker peptide, the variable region of the heavy chain of e23, and amino acids 253–613 of PE. The chimeric protein was expressed in *E. coli* and purified. The resulting protein was >70% pure as judged by SDS/PAGE (data not shown).

Cytotoxicity of e23(Fv)PE40.

e23(Fv)PE40 was tested on BT474 breast cancer cells and was found to inhibit protein synthesis in a dose-dependent manner with an $ID_{50}$ of 1.5 ng/ml (FIG. 10, Table 1). The cytotoxic activity was blocked by competition with excess native e23, demonstrating the specificity of e23(Fv)PE40 for erbB-2-containing cells (FIG. 10). Another anti-erbB-2 monoclonal antibody, e21, which binds to a different site, had no effect on the toxicity of e23(Fv)PE40 (data not shown). In the same experiment, e23-LysPE40, a chemical conjugate comprising e23 chemically conjugated to PE40, had an $ID_{50}$ of 12 ng/ml (FIG. 10, Table 1). The activity of e23(Fv)PE40 was assayed on several cell lines expressing erbB-2 and compared with that of the chemical conjugate, e23-Lys40 (Table 1). On all four target cells, e23(Fv)PE40 was active and the $ID_{50}$ values on a molar basis were 2- to 3-fold lower than those of e23-LysPEA0. Both molecules had very little activity on KB cells, showing their specificity for erbB-2-expressing cells.

Derivatives of e23(Fv)PE40.

It is known that when the five carboxy terminal amino acids of the Pseudomonas exotoxin variant PE40 are replaced by KDEL that this results in molecules that have 3- to 10-fold higher cytotoxic activities See Maram et al, *J. Biol. Chem.*, (1991), 266, 17376–17381. Also, deleting part of domain Ib of PE, specifically amino acids 365–380, thereby deleting a disulfide bond, does not result in any loss of activity of several fusion proteins including TGFα-PE40, anti-Tac(Fv)-PE40, and B3(Fv)-PE40, Brinkmann et al, *Proc. Nat'l. Acad. Sci.*, (1991), 88, 8616–8620; Siegall et al, *J. Biol. Chem.*, (1989), 264, 14256–14261. Since mixed disulfide bonds can form during the renaturation of recombinant proteins, we thought it would be helpful to delete this region. To explore the possibility of making a much more active derivative of e23(Fv)PE40, we made three new constructions: (i) e23(Fv)PE40KDEL, where the five carboxyl terminal amino acids of PE40 are replaced by KDEL; (ii) e23(Fv)PE38, in which amino acids 365–380 have been deleted from e23(Fv)PE40 but the carboxyl terminus is not altered; and (iii) e23(Fv)PE38KDEL, where the five C-terminal amino acids are replaced by KDEL in e23(Fv)PE38.

These derivatives are diagramed in FIG. 11. The chimeric proteins were also purified to >70% purity and tested for cytotoxic activity on target cells. As shown in FIG. 12, all of the new derivatives inhibited the protein synthesis of BT474 cells in a dose-dependent manner, with e23(Fv)PE38KDEL being the most active. Table 2 summarizes the $ID_{50}$ values of the e23(Fv)PE40 derivatives on various cell lines. On all three target cell lines, e23(Fv)PE38KDEL, was found to be the most active. e23(Fv)PE38KDEL was 6- to 10-fold more active than e23(Fv)PE40 (Table 2). None of the proteins had any cytotoxicity on KB cells, a cell line that does not overexpress erbB-2. In the presence of excess e23, the cytotoxic activity of all derivatives was abolished (data not shown). The binding activity of e23(Fv)PE38KDEL was monitored in a competition binding assay. As shown in FIG. 9, e23(Fv)PE38KDEL was able to compete with homologous e23 Fab for binding, but a higher concentration was required than for e23(Fv). This result is consistent with either a lower overall affinity of e23(Fv)PE38KDEL or the purified protein being a mixture of active and inactive species. Current purification methods for e23(Fv)PE38KDEL do not allow us to separate forms on the basis of binding activity. To verify the binding activity of the e23(Fv), we conducted a similar competition binding assay and found that e23 Fab binds with slightly lower affinity than intact antibody and monomeric Fab produced from e23 (FIG. 9).

Growth Inhibition of Human Tumors in a Nude Mouse Model.

The selective toxicity of the e23(Fv)PE38KDEL to cells overexpressing erbB-2 encouraged us to attempt to treat human tumor cells growing in nude mice. The human gastric cancer cell line N87 has been shown to overexpress erbB-2 protein at high levels as a result of gene amplification, and N87 cells grow well as a subcutaneous tumor in immunocomprised mice Kaspyrzyk et al, *Cancer Res.*, (1992), 52, 2771–2776. Injections of $5 \times 10^6$ cells on day 0 were followed by six intravenous treatments over 3 days, starting on day 10. Immunotoxin treatment inhibited growth of established tumors (FIG. 13). No animal deaths were observed at doses of 2 μg. Equivalent amounts of either e23 Fab, e23 SC(Fv) (data not shown), or LysPE38KDEL had no effect on tumor growth. Nonspecific toxicity was assayed by monitoring the animal weight; no weight loss was observed at doses of 2 μg.

TABLE 1

Comparison of activity of e23(Fv)PE40 and chemical conjugates on various human cells lines $ID_{50}$ ng/ml (pM)

| Cells | e23(Fv)PE40 | e23-LysPE40 | Relative activity* |
|---|---|---|---|
| BT474 | 1.5 (23) | 12 (63) | 0.37 |
| N87 | 3.5 (54) | 24 (126) | 0.43 |
| SK-OV-3 | 22.0 (338) | 180 (947) | 0.36 |
| SK-Br-3 | 32.0 (492) | 180 (947) | 0.52 |
| A431 | 170.0 (2615) | >500 (>2631) | NC |

*Ratio of $ID_{50}$(pM) of e23(Fv)PE40 to $ID_{50}$ of e23-LysPE40 on the same cell line.
NC, not calculated.

TABLE 2

Activity of e23(Fv)PE40 and derivatives on various human cell lines

| Protein | BT474 | N87 | SK-OV-3 | KB |
| --- | --- | --- | --- | --- |
| e23(Fv)PE40 | 3 | 8 | 80 | >500 |
| e23(Fv)PE40KDEL | 1.6 | 3.8 | 22 | >500 |
| e23(Fv)PE40KDEL | 3.6 | 3.7 | 62 | >500 |
| e23(Fv)PE38KDEL | 0.18 | 1.2 | 5 | >500 |

Based upon the above results, it is expected that the subject erbB-2 immunotoxins, most particularly e23(Fv)PE38KDEL should be suitable for treatment of cancers associated by the overexpression of $gp185^{erbB-2}$ which occurs, e.g., in about 30% of adenocarcinomas of the breast, stomach, lung and ovary. Direct evidence supporting this conclusion is provided by the results showing inhibition of tumor growth in nude mice.

EXAMPLE 11

The following experiment analyzes the expression of the antigen recognized by murine monoclonal antibody e23 on a panel of normal human tissues, using cryostat-cut frozen tissue sections and the avidin-biotin immunoperoxidase technique. These studies were conducted at the highest concentration of antibody that does not show non-specific binding. This allows for the detection of all levels of cross-reactivity in different tissues. In addition, fixation analyses to establish the best combination of antigenic showing intensity and morphological preservation was performed.

MATERIAL AND METHODS

Source of the tissues

Histologically normal adult human tissues were obtained from surgical pathology and autopsy specimens. Fresh tissues were embedded in cryomolds of OCT compound (Miles Laboratories, Inc., Naperville, Ill.), frozen, and stored at −70° C. until needed. All tissues were used as frozen tissue sections from IMPATH's frozen tissue bank, and were well-preserved histologically.

Reagents e23 was used at a concentration of 1.0 mg/ml, and was used diluted in phosphate buffered saline (PBS, NACl-8.54 gms and $NaPo_4$-1.46 gms per liter, pH=7.2–7.4) (DIFCO Laboratories, Detroit, Mich.) containing 2% bovine serum albumin (BSA). e23 was received on wet ice and stored at 4° C.

Purified mouse IgG1 (Coulter Immunology, Hialeah, Fla.), was used as the negative control, diluted in 2% BSA/PBS to the same working concentration as Antibody e23.

Biotinylated horse anti-mouse IgG (heavy + light chains specific) affinity purified antibodies (1:200 dilution in PBS) (Vector Laboratories, Inc., Burlingame, Calif.) were used as a secondary antibody.

Avidin-biotin-peroxidase complexes (1:50 dilution in PBS) (Vector Laboratories, Inc., Burlingame, Calif.) were used as the labeling reagent.

Immunohistochemistry

Immunoperoxidase Techniques: Immunohistochemical studies were performed using the Avidin-Biotin Immunoperoxidase technique. To assure that tissue sections adhere, slides were coated with 0.005% Poly-L-Lysine solution in deionized water (Sigma Chemical Co., St. Louis, Mo.). Frozen sections were cryostat-cut (4–8 microns thick), air dried and fixed in 95% ethanol, then bathed in PBS.

Endogenous peroxidase activity was blocked with a 10 minute 0.3% hydrogen peroxide incubation.

To reduce endogenous biotin content, all tissues were washed several times in PBS, then incubated with a solution of avidin (Vector Labs) for 15 minutes at room temperature, washed in PBS, incubated with a solution of biotin (Vector Labs) for 15 minutes at room temperature, and washed in PBS.

Tissue sections were then incubated for 10 minutes with suppressor serum. Suppressor serum consisted of normal horse serum (NHS) (Jackson ImmunoResearch Labs, West Grove, Pa.) diluted to 5% with PBS containing 2% BSA.

Tissue sections were incubated with the primary antibody for 30 minutes at room temperature. Sections were then washed, incubated with biotinylated horse anti-mouse IgG antibodies for 20 minutes, washed in PBS, incubated with avidin-biotin-peroxidase complexes for 20 minutes, then washed in PBS.

The peroxidase reaction was performed by incubating tissue sections for 2–5 minutes with 3,3-diaminobenzidine-tetrahydrochloride (DAB) (Sigma Chemical Co., St. Louis, Mo.). Tissue sections were thoroughly washed, counterstained with Harris hematoxylin, alehydrated through graded alcohols and xylenes, and mounted with permaslip (Alba Scientific, St. Louis, Mo.).

Tissues that demonstrated high levels of background staining with the negative control antibody were repeated, utilizing more extensive washing and avidin-biotin blocking.

Controls erbB-2 positive human breast carcinoma (92-31-626) was used as positive control for Antibody e23; erbB-2 negative human breast carcinoma (92-31-625) was used as the negative control tissue for e23. Both control tissues were supplied by Oncologix, Inc. Negative controls consisted of substitution of the primary antibody with purified mouse IgG 1, used at the same working concentration as test antibody e23.

Fixation

The purpose of the fixation analysis is to establish the conditions which provide the optimal combination of antigenie staining intensity and morphological preservation. Frozen tissues used in our studies are fixed after they have been sectioned, and fixatives are only used in subsequent studies if the staining intensity is better than in unfixed sections. For this study, positive control tissue fixed with four fixative reagents were compared to unfixed tissue. These fixatives included 10% neutral buffered formalin, acetone (2°–8° C.), methyl/acetone (1:1 V/V; 2°–8° C.) and 95% ethanol. Fixation in 95% ethanol gave optimal results for e23.

Titration

The purpose of the titration analysis is to determine the highest concentration of the antibody that can be used for the study without non-specific binding. This allows for detection of all levels of cross-reactivity in different tissues. This analysis showed a concentration of 10.0/µg /ml to be optimal.

GLP

All aspects of the study were conducted in adherence to the FDA Good Laboratory Practices regulations.

The results of this analysis are set forth on the following pages.

RESULTS OF SPECIFICITY ANALYSIS
Antibody e23
Summary of Reactivity on Normal Tissues

|  | Tested Positive/Total | Range of Reactivity (0 to 3+) |
|---|---|---|
| Neg. Control Tissue- Breast Carcinoma | 0 | 0 |
| Pos. Control Tissue- Breast Carcinoma | 90–100% of the tumor cells | 3+ |
| Adrenal: | | |
| Cortex | 0/3 | 0 |
| Medulla | 0/3 | 0 |
| Bladder: | 3/3 | +/− to 3+ |
| Bone Marrow: | 0/3 | 0 |
| Peripheral Blood Cells: | 0/3 | 0 |
| Brain: | | |
| Neuroglia | 0/1 | 0 |
| Neurons | 0/1 | 0 |
| Brain Cerebellum: | | |
| Neuroglia | 0/4 | 0 |
| Neurons | 0/4 | 0 |
| Brain Cortex: | | |
| Neuroglia | 0/2 | 0 |
| Neurons | 0/2 | 0 |
| Breast: | | |
| Acini | 3/3 | 1+ to 3+ |
| Ducts | 3/3 | 1+ to 3+ |
| Cervix: | | |
| Endocervix | 3/3 | 2+ to 3+ |
| Exocervix | 3/3 | 1 + F to 3+ |
| Esophagus: | | |
| Squamous epithelium | 2/3 | 1+ to 3+ |
| Glands | 2/2[1] | 3+ |
| Eye: | 0/3 | 0 |
| Heart: | 0/3 | 0 |
| Kidney: | | |
| Glomerulus | 0/3 | 0 |
| Tubules | 0/3 | 0 |
| Collecting Tubules | 0/3 | 0 |
| Large Intestine: | 3/3 | +/− |
| Liver: | | |
| Hepatocytes | 0/3 | 0 |
| Bile ducts | 0/3 | 0 |
| Kupffer cells | 0/3 | 0 |
| Lung: | | |
| Bronchial cells | 3/3 | 2+ |
| Alveolar cells | 3/3 | 1+ to 2+ |
| Lymph Node: | 0/3 | 0 |
| Muscle, skeletal: | 0/3 | 0 |
| Ovary: | 0/3* | 0 |

*Mesothelial cells reactive (2–3+) in 1 of 3 specimens; ovary negative.

| Pancreas: | | |
|---|---|---|
| Endo. Cells | 0/3 | 0 |
| Exo. Cells | 0/3 | 0 |
| Ducts | 0/3 | 0 |
| Parathyroid: | 0/3 | 0 |
| Parotid Gland: | 3/3 | 1+ to 2+ |
| Pituitary: | 0/3 | 0 |
| Prostate: | 3/3* | 1+ to 2+ |

*Stromal cells (fibroblasts) are reactive (2–3+) in 3 of 3 specimens.

| Skin: | | |
|---|---|---|
| Epidermis | 3/3 | 1+ |
| Adnexa | 3/3 | 1+ |
| Small intestine: | 3/3 | 1+ to 3+ |

RESULTS OF SPECIFICITY ANALYSIS
Antibody e23
Summary of Reactivity on Normal Tissues

|  | Tested Positive/Total | Range of Reactivity (0 to 3+) |
|---|---|---|
| Spinal Cord: | | |
| Neuropil | 0/3 | 0 |
| Neurons | 0/3 | 0 |
| Spleen: | 0/3 | 0 |
| Stomach: | 3/3 | 1 + F |
| Skeletal muscle: | 0/3 | 0 |
| Thymus: | 0/2 | 0 |
| Testis: | | |
| Germinal cells | 0/3 | 0 |
| Stromal cells | 0/3 | 0 |
| Thyroid: | 0/3 | 0 |
| Tonsil: | 0/3 | 0 |
| Uterus: | | |
| Endometrium | 2/2[2] | 1+ to 2+ |
| Myometrium | 0/3 | 0 |
| Stromal cells | 0/3 | 0 |

[1]Glands not seen in 1 of 3 specimens.
[2]Endometrium not seen in 1 of 3 specimens.

Murine monoclonal antibody e23 was supplied by Oncologix, Inc. to IMPATH for analysis of immunoreactivity with a selected panel of normal human tissues. Antibody e23 is of the IgG 1 subclass and was supplied at a concentration of 1.0 mg/ml. Fixation analysis indicated that the optimal fixative for Antibody e23 was 95% ethanol. Using 95% ethanol as the fixative of choice, a titration analysis was run using the positive control tissue, human breast carcinoma (92-31-626), supplied by Oncologix, Inc. The purpose of the titration analysis is to determine the highest concentration of the antibody that can be used for the study without non-specific binding. This allows for detection of all, including low, levels of cross-reactivity of the antibody in different tissues. Since the components that give rise to non-specific binding are not tissue specific, the titration analysis is done on the positive control tissue. Titration analysis with e23 indicated that the optimal working concentration for the antibody was 10.0 µg/ml in IMPATH's test system.

e23 was found to have a very restricted pattern of reactivity. Positive reactivity was observed in tissues of simple, stratified and squamous epithelial origin. e23 showed positive reactivity with cells of the bladder, breast, cervix, esophagus, large and small intestines, bronchial and alveolar cells of the lung, parotid gland, prostate, skin and endometrium of the uterus. The reactivity with e23 was restricted to the membrane of these epithelial cells; the intensity of reactivity varied from equivocal to strong.

All cells of lymphoid origin including bone marrow, peripheral blood, lymph node, spleen, and tonsil were unreactive with the test antibody.

Immunoreactivity was also not seen in cells of neuroectodermal origin including those in the brain, spinal cord, and peripheral nerve. Mesenchymal elements such as skeletal and smooth muscle cells, endothelial cells, as well as polymorphonuclear inflammatory cells were negative with antibody e23. Stromal cells of possible mesenchymal origin present in the prostate were reactive with antibody e23.

In summary, the reactivity observed with antibody e23 was restricted to the membrane of simple, stratified, and squamous epithelial cells in normal human tissues. Thus, given its minimal reactivity with normal tissues, e23 and its corresponding single chain antibodies, or humanized antibodies derived therefrom, and antibodies having the immunobinding characteristics thereof should be well suited for use as a diagnostic or therapeutic agent for patients exhibiting cancers associated by gp185$^{erbB-2}$ overexpression which include certain highly malignant tumors, such as adenocarcinoma of the stomach, lung, breast and ovary.

The reactivity of e23 and e21 was then compared for a number of primate tissues. The results of this comparison are set forth on the following page. The results therein clearly demonstrate that e23 exhibits substantially lower reactivity with normal primate tissues than e21. Given its lower reactivity with normal tissues, it is expected that e23 should function as a better diagnostic and/or therapeutic agent than e21. In particular, it is expected that e23 should provide for fewer false positive diagnoses and lesser adverse reactions to normal human tissues.

| Comparison of e23 and e21 Antibodies | | |
|---|---|---|
| | e23 | e21 |
| Western Blot | − | − |
| Immunoprecipitation | + | + |
| ELISA | + | + |
| Immunohistochemistry Formalin Fixed | − | + |
| Immunohistochemistry Frozen | + | + |
| Cynomolgus and Baboon Esophagus | luminal edge cells of epithelium, membrane | epithelial cells, membrane Periferal nerve cells |
| Cynomolgus and Baboon Breast | delicate fibroblast staining | ductal epithelium 3+ keratinocytes (skin) fibroblasts 2+ perineurium 2+ endothelim 1–2+ endoneurium 1+ |
| Cynomolgus brain | cerebellum - no staining cortex - no staining | cerebellum - no staining cortex - arachnoid 2+ - dura 2+ |
| Cynomolgus bladder | +/− | +, Membrane |

We claim:

1. A single chain antibody which binds to erbB-2 which comprises the variable heavy and light domains of a monoclonal antibody selected from the group consisting of e21 having ATCC Accession No. HB11602 and e23 having ATCC Accession No. HB11601.

2. The single chain antibody of claim 1 which comprises the amino acid sequence set forth in SEQ ID NO: 1 or SEQ ID NO: 2.

3. An immunoconjugate comprising the single chain antibody of claim 1 bound to a cytotoxic moiety or a label.

4. An immunoconjugate comprising the single chain antibody of claim 2 bound to a cytotoxic moiety or a label.

5. The immunoconjugate of claim 3 or claim 4 wherein said label is selected from the group consisting of a fluorescent label, an enzymatic label, and a radiolabel.

6. A diagnostic composition suitable for in vitro assaying for gp185$^{erbB-2}$ which comprises a diagnostically effective amount of at least one of the single chain antibodies according to claim 1, in a carrier.

7. A diagnostic composition suitable for in vitro assaying for gp185$^{erbB-2}$ which comprises a diagnostically effective amount of the immunoconjugate of claim 3, in a carrier.

8. The diagnostic composition of claim 7, wherein the single chain antibody comprises the amino acid sequence set forth in SEQ ID NO: 1 or SEQ ID NO: 2.

9. The diagnostic composition of claim 6, wherein the single chain antibody comprises the amino acid sequence set forth in SEQ ID NO: 1 or SEQ ID NO: 2.

10. The diagnostic composition of claim 6, wherein the single chain antibody is fused to an enzyme or fragment or derivative thereof comprising enzymatic activity.

11. The diagnostic composition of claim 10, wherein the enzyme comprises horseradish peroxdase or alkaline phosphatase.

12. The diagnostic composition of claim 6, wherein the single chain antibody comprises the amino acid sequence set forth in SEQ ID NO: 1 or SEQ ID NO: 2.

\* \* \* \* \*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 711 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..711

( i x ) FEATURE:
        ( A ) NAME/KEY: misc_feature
        ( B ) LOCATION: 162
        ( D ) OTHER INFORMATION: /note= "Nucleotide 162 wherein G is K =G or T(U)."

( x i ) SEQUENCE DESCRIPTION: SEQ ID NO:1:

```
ATG GAC CTG CAG CTG ACC CAG TCT CCA GCA ATC CTG TCT GCA TCT CCA        48
Met Asp Leu Gln Leu Thr Gln Ser Pro Ala Ile Leu Ser Ala Ser Pro
 1               5                  10                  15

GGG GAG AAG GTC ACA ATG ACT TGC AGG GCC ACC CCA AGT GTA AGT TAC        96
Gly Glu Lys Val Thr Met Thr Cys Arg Ala Thr Pro Ser Val Ser Tyr
            20                  25                  30

ATG CAC TGG TAT CAG CAG AAG CCA GGA TCC TCC CCC AAA CCT TGG ATT       144
Met His Trp Tyr Gln Gln Lys Pro Gly Ser Ser Pro Lys Pro Trp Ile
        35                  40                  45

TAT ACC ACA TCC AAC CTG GCT TCT GGA GTC CCT GCT CGC TTC AGT GGC       192
Tyr Thr Thr Ser Asn Leu Ala Ser Gly Val Pro Ala Arg Phe Ser Gly
    50                  55                  60

GGT GGG TCT GGG ACC TCT TAC TCT CTC ACA GTC AGC AGA GTG GAG GCT       240
Gly Gly Ser Gly Thr Ser Tyr Ser Leu Thr Val Ser Arg Val Glu Ala
65                  70                  75                  80

GAA GAT GCT GCC ACT TAT TAC TGC CAG CAG TGG AGT CGT AGC CCA CCC       288
```

| | | | | | | | | | | | | | | | |
|---|---|---|---|---|---|---|---|---|---|---|---|---|---|---|---|
| Glu | Asp | Ala | Ala | Thr | Tyr | Tyr | Cys | Gln | Gln | Trp | Ser | Arg | Ser | Pro | Pro |
| | | | | 85 | | | | | 90 | | | | | 95 | |

ACG TTC GGA GGG GGG TCC AAG CTG GAA ATA AAA GGT TCT ACC TCT GGT  336
Thr Phe Gly Gly Gly Ser Lys Leu Glu Ile Lys Gly Ser Thr Ser Gly
              100               105               110

TCT GGT AAA TCT TCT GAA GGT AAA GGT GTG CAG CTG CAG GAG TCA GGA  384
Ser Gly Lys Ser Ser Glu Gly Lys Gly Val Gln Leu Gln Glu Ser Gly
         115               120               125

CCT GAG GTG GTG AAG CCT GGA GGT TCA ATG AAG ATA TCC TGC AAG ACT  432
Pro Glu Val Val Lys Pro Gly Gly Ser Met Lys Ile Ser Cys Lys Thr
    130               135               140

TCT GGT TAC TCA TTC ACT GGC CAC ACC ATG AAC TGG GTG AAG CAG AGC  480
Ser Gly Tyr Ser Phe Thr Gly His Thr Met Asn Trp Val Lys Gln Ser
145               150               155               160

CAT GGA AAG AAC CTT GAG TGG ATT GGA CTT ATT AAT CCT TAC AAT GGT  528
His Gly Lys Asn Leu Glu Trp Ile Gly Leu Ile Asn Pro Tyr Asn Gly
              165               170               175

GAT ACT AAC TAC AAC CAG AAG TTC AAG GGC AAG GCC ACA TTT ACT GTA  576
Asp Thr Asn Tyr Asn Gln Lys Phe Lys Gly Lys Ala Thr Phe Thr Val
         180               185               190

GAC AAG TCG TCC AGC ACA GCC TAC ATG GAG CTC CTC AGT CTG ACA TCT  624
Asp Lys Ser Ser Ser Thr Ala Tyr Met Glu Leu Leu Ser Leu Thr Ser
    195               200               205

GAG GAC TCT GCA GTC TAT TAC TGT GCA AGG AGG GTT ACG GAC TGG TAC  672
Glu Asp Ser Ala Val Tyr Tyr Cys Ala Arg Arg Val Thr Asp Trp Tyr
210               215               220

TTC GAT GTC TGG GGC GCA GGG ACC ACG GTC ACC GTC TCC              711
Phe Asp Val Trp Gly Ala Gly Thr Thr Val Thr Val Ser
225               230               235

( 2 ) INFORMATION FOR SEQ ID NO:2:

( i ) SEQUENCE CHARACTERISTICS:
        ( A ) LENGTH: 720 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..720

( x i ) SEQUENCE DESCRIPTION: SEQ ID NO:2:

ATG CAG CTG ACC CAG TCT CCA GCA ATC ATG TCT GCA TCT CCA GGG GAA  48
Met Gln Leu Thr Gln Ser Pro Ala Ile Met Ser Ala Ser Pro Gly Glu
  1               5               10               15

AAG GTC ACC ATG ACC TGC AGT GCC AGC TCA AGT GTA AGT AAC ATG CAC  96
Lys Val Thr Met Thr Cys Ser Ala Ser Ser Ser Val Ser Asn Met His
              20               25               30

TGG TAT CAG CAG AAG TCA AGC ACC TCC CCC AAA CTC TGG GTT TAT GAC  144
Trp Tyr Gln Gln Lys Ser Ser Thr Ser Pro Lys Leu Trp Val Tyr Asp
         35               40               45

ACA TCC AAA CTG GCT TCT GGA GTC CCA GGT CGC TTC AGT GGC AGT GGG  192
Thr Ser Lys Leu Ala Ser Gly Val Pro Gly Arg Phe Ser Gly Ser Gly
    50               55               60

TCT GGA AAC TCT TAC TCT CTC ACG ATC AGC AGC ATG GAG GCT GAA GAT  240
Ser Gly Asn Ser Tyr Ser Leu Thr Ile Ser Ser Met Glu Ala Glu Asp
65               70               75               80

GCT GCC ACT TAT TAT TGT TAT CAG GGG AGT GGG TAC CCA TTC ACG TTC  288
Ala Ala Thr Tyr Tyr Cys Tyr Gln Gly Ser Gly Tyr Pro Phe Thr Phe
              85               90               95

| | | | | | | | | | | | | | | | | |
|---|---|---|---|---|---|---|---|---|---|---|---|---|---|---|---|---|
| GGC | TCG | GGG | ACA | AAG | TTG | GAA | ATA | AAA | GGT | TCT | ACC | TCC | GGA | TCT | GGT | 336 |
| Gly | Ser | Gly | Thr | Lys | Leu | Glu | Ile | Lys | Gly | Ser | Thr | Ser | Gly | Ser | Gly | |
| | | | 100 | | | | | 105 | | | | | 110 | | | |
| AAA | TCT | TCT | GAA | GGT | AAA | GGT | GTG | CAG | CTG | CAG | CAG | TCT | GGG | GTT | GAG | 384 |
| Lys | Ser | Ser | Glu | Gly | Lys | Gly | Val | Gln | Leu | Gln | Gln | Ser | Gly | Val | Glu | |
| | | 115 | | | | | 120 | | | | | 125 | | | | |
| CTT | GTC | CGA | GGA | GGG | GCC | TTA | GTC | AAG | TTG | TCC | TGC | AAA | GCT | TCT | GAC | 432 |
| Leu | Val | Arg | Gly | Gly | Ala | Leu | Val | Lys | Leu | Ser | Cys | Lys | Ala | Ser | Asp | |
| | 130 | | | | | 135 | | | | | 140 | | | | | |
| TTC | AAC | ATT | AAA | GAC | TAT | TAT | ATC | CAC | TGG | GTG | AAG | CAG | AGG | CCT | GAA | 480 |
| Phe | Asn | Ile | Lys | Asp | Tyr | Tyr | Ile | His | Trp | Val | Lys | Gln | Arg | Pro | Glu | |
| 145 | | | | | 150 | | | | | 155 | | | | | 160 | |
| CAG | GGC | CTG | GAA | TGG | ATT | GGA | TGG | ATT | CAT | CCT | GAG | AAT | GGT | AAT | ACT | 528 |
| Gln | Gly | Leu | Glu | Trp | Ile | Gly | Trp | Ile | His | Pro | Glu | Asn | Gly | Asn | Thr | |
| | | | | 165 | | | | | 170 | | | | | 175 | | |
| GTA | TAT | GAC | CCG | AAA | TTC | CAG | GGC | AAG | GCC | AGT | ATA | ACA | GCA | GAC | ACA | 576 |
| Val | Tyr | Asp | Pro | Lys | Phe | Gln | Gly | Lys | Ala | Ser | Ile | Thr | Ala | Asp | Thr | |
| | | | 180 | | | | | 185 | | | | | 190 | | | |
| TCC | TCC | AAC | GCG | GCC | TAC | CTT | CAG | CTC | AGC | AGC | CTG | ACA | TCT | GAG | GAC | 624 |
| Ser | Ser | Asn | Ala | Ala | Tyr | Leu | Gln | Leu | Ser | Ser | Leu | Thr | Ser | Glu | Asp | |
| | | 195 | | | | | 200 | | | | | 205 | | | | |
| ACT | GCC | GTC | TAT | TAC | TGT | GCT | TCT | TAT | TAC | TAC | TAT | AGT | GCT | TAC | TAT | 672 |
| Thr | Ala | Val | Tyr | Tyr | Cys | Ala | Ser | Tyr | Tyr | Tyr | Tyr | Ser | Ala | Tyr | Tyr | |
| | 210 | | | | | 215 | | | | | 220 | | | | | |
| GCT | ATG | TAC | TAC | TGG | GGT | CAA | GGA | ACC | TCG | GTC | ACC | GTC | TCC | TCA | TAA | 720 |
| Ala | Met | Tyr | Tyr | Trp | Gly | Gln | Gly | Thr | Ser | Val | Thr | Val | Ser | Ser | | |
| 225 | | | | | 230 | | | | | 235 | | | | | 240 | |

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CACGTCGACA TTCAGCTGAC CCACTCTCCA               30

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GATGGATCCA GTTGGTGCAG CATC                     24

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 21

(D) OTHER INFORMATION: /note= "N =inosine."

(ix) FEATURE:
    (A) NAME/KEY: misc_feature
    (B) LOCATION: 26
    (D) OTHER INFORMATION: /note= "W =A or T."

(xi) SEQUENCE DESCRIPTION: SEQ ID NO:5:

```
CGGAATTTCA GGTTCTGCAG NAGTCWGG                                              28
```

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
AGCGGATCCA GGGGCCAGTG GATAGAC                                               27
```

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
CGAGATGAGT CCAGCTGACC CAGTCTC                                               27
```

(2) INFORMATION FOR SEQ ID NO:8:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GAAGATTTAC CAGAACCAGA GGTAGAACCT TTTATTTCCA GCTTGGA                         47
```

(2) INFORMATION FOR SEQ ID NO:9:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
CTGGTTCTGG TAAATCTTCT GAAGGTAAAG GTGTGCAGCT GCAGGAG                         47
```

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (  i  i  ) MOLECULE TYPE: DNA (genomic)

(  x  i  ) SEQUENCE DESCRIPTION: SEQ ID NO:10:

CGAGTGCAAG CTTAGGAGAC GGTGACCGT 29

( 2 ) INFORMATION FOR SEQ ID NO:11:

(  i  ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear (  i  i  ) MOLECULE TYPE: peptide (  x  i  ) SEQUENCE DESCRIPTION: SEQ ID NO:11:

Gly  Ser  Thr  Ser  Gly  Ser  Gly  Lys  Ser  Ser  Glu  Gly  Lys  Gly
1                   5                        10